United States Patent
Purse et al.

(10) Patent No.: US 11,981,702 B2
(45) Date of Patent: *May 14, 2024

(54) COMPOUNDS FOR FLUORESCENCE SENSING OF DUPLEX FORMATION

(71) Applicant: San Diego State University Research Foundation, San Diego, CA (US)

(72) Inventors: Byron W. Purse, San Diego, CA (US); Dillon Burns, San Diego, CA (US); Kristine Teppang, San Diego, CA (US); Raymond Lee, San Diego, CA (US); Melissa Lokensgard, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/943,682

(22) Filed: Sep. 13, 2022

(65) Prior Publication Data

US 2023/0094737 A1 Mar. 30, 2023

Related U.S. Application Data

(63) Continuation of application No. 16/346,708, filed as application No. PCT/US2017/060776 on Nov. 9, 2017, now Pat. No. 11,447,519.

(60) Provisional application No. 62/533,897, filed on Jul. 18, 2017, provisional application No. 62/420,347, filed on Nov. 10, 2016.

(51) Int. Cl.
| | | |
|---|---|---|
| *C07H 19/24* | (2006.01) | |
| *C09K 11/06* | (2006.01) | |
| *C12Q 1/68* | (2018.01) | |
| *C12Q 1/682* | (2018.01) | |
| *C12Q 1/686* | (2018.01) | |
| *G01N 21/77* | (2006.01) | |

(52) U.S. Cl.
CPC .............. *C07H 19/24* (2013.01); *C09K 11/06* (2013.01); *C12Q 1/682* (2013.01); *C12Q 1/686* (2013.01); *G01N 21/77* (2013.01); *C09K 2211/1018* (2013.01); *G01N 2021/7786* (2013.01)

(58) Field of Classification Search
CPC .. C07H 19/24; C09K 11/06; C09K 2211/1018
See application file for complete search history.

(56) References Cited

U.S. PATENT DOCUMENTS

| | | | |
|---|---|---|---|
| 6,005,096 A | 12/1999 | Matteucci et al. | |
| 6,414,127 B1 | 7/2002 | Lin et al. | |
| 7,511,125 B2 | 3/2009 | Lin et al. | |
| 8,507,661 B2 | 8/2013 | Manoharan et al. | |
| 8,975,389 B2 | 3/2015 | Manoharan et al. | |
| 9,725,479 B2 | 8/2017 | Manoharan et al. | |
| 10,233,448 B2 | 3/2019 | Maier et al. | |
| 2003/0158403 A1 | 8/2003 | Manoharan et al. | |
| 2011/0130440 A1 | 6/2011 | Manoharan et al. | |
| 2013/0130378 A1 | 5/2013 | Manoharan et al. | |
| 2013/0203836 A1 | 8/2013 | Rajeev et al. | |

FOREIGN PATENT DOCUMENTS

WO 9507918 A2 3/1995

OTHER PUBLICATIONS

Aitken et al., "An Oxygen Scavenging System for Improvement of Dye Stability in Single-Molecule Fluorescence Experiments," Biophys J., 94(5):1826-1835, Mar. 2008.
Compound Summary for CID 59089368, Pubchem, Dec. 2017.
International Search Report and Written Opinion of the ISA/US in PCT/US2017/060776 dated Mar. 5, 2018; 9pgs.
Malyshev et al., "A Semi-synthetic Organism with an Expanded Genetic Alphabet," Nature, 509(7500):385-388, May 2014.
Michalet et al., "Development of New Photon-Counting Detectors for Single-Molecule Fluorescence Microscopy," Philos Trans R Soc Lond B Biol Sci., 368(1611):1-22, Dec. 2012.
Narayanaswamy et al., "A Thiazole Coumarin (TC) Turn-On Fluorescence Probe for AT-Base Pair Detection and Multipurpose Applications in Different Biological Systems," Sci. Rep., 4(6476): 1-10; Sep. 2014.
Ray et al., "Application of Kinase Bypass Strategies to Nucleoside Antivirals," Antiviral Res., 92(2):277-291, Nov. 2011.
Rodgers et al., "Functionalized Tricyclic Cytosine Analogues Provide Nucleoside Fluorophores with Improved Photophysical Properties and a Range of Solvent Sensitivities," Chemistry, 20(7):2010-2015, Feb. 2014.
Sharma et al., "Antisense Oligonucleotides: Modifications and Clinical Trials," MedChemComm, 10:1454-1471, Oct. 2014.

(Continued)

*Primary Examiner* — Jezia Riley
(74) *Attorney, Agent, or Firm* — Haukaas Fortius PLLC; Michael Haukaas

(57) ABSTRACT

Herein reported are new tricyclic cytidine compounds, such as 8-diethylamino-tC (8-DEA-tC), that respond to DNA and/or RNA duplex formation with up to a 20-fold increase in fluorescent quantum yield as compared with the free nucleoside, depending on neighboring bases. This turn-on response to duplex formation is by far the greatest of any reported nucleoside analogue that can participate in Watson-Crick base pairing. Measurements of the quantum yield of 8-DEA-tC mispaired with adenosine and, separately, opposite an abasic site show that there is almost no fluorescence increase without the formation of correct Watson-Crick hydrogen bonds. Kinetic isotope effects from the use of deuterated buffer show that the duplex protects 8-DEA-tC against quenching by excited state proton transfer. DFT calculations provide a rationale for the observed photophysical properties that is dependent on duplex integrity and the electronic structure of the analogue.

20 Claims, 14 Drawing Sheets

Specification includes a Sequence Listing.

(56) References Cited

OTHER PUBLICATIONS

Turner et al., "Synthesis of Fluorescence Turn-On DNA Hybridization Probe using the DEAtC 2'-deoxycytidine Analogue," Curr Protoc Nucleic Acid Chem., 75(1):e59, Dec. 2018.

SEQUENCE LISTING

Sequence total quantity: 41
SEQ ID NO: 1         moltype =    length =
SEQUENCE: 1
000

-continued

```
SEQ ID NO: 2              moltype =     length =
SEQUENCE: 2
000

SEQ ID NO: 3              moltype =     length =
SEQUENCE: 3
000

SEQ ID NO: 4              moltype =     length =
SEQUENCE: 4
000

SEQ ID NO: 5              moltype =     length =
SEQUENCE: 5
000

SEQ ID NO: 6              moltype =     length =
SEQUENCE: 6
000

SEQ ID NO: 7              moltype =     length =
SEQUENCE: 7
000

SEQ ID NO: 8              moltype =     length =
SEQUENCE: 8
000

SEQ ID NO: 9              moltype =     length =
SEQUENCE: 9
000

SEQ ID NO: 10             moltype = DNA  length = 10
FEATURE                   Location/Qualifiers
misc_feature              1..10
                          note = SYNTHETIC DNA OLIGONUCLEOTIDE
modified_base             6
                          mod_base = OTHER
                          note = c is 8-Diethylamino-tricyclic-2 -deoxy-
                           -D-ribonucleoside
source                    1..10
                          mol_type = other DNA
                          organism = synthetic construct
SEQUENCE: 10
cgcagcatcg                                                                 10

SEQ ID NO: 11             moltype = DNA  length = 10
FEATURE                   Location/Qualifiers
misc_feature              1..10
                          note = Synthetic DNA Oligonucleotide
modified_base             6
                          mod_base = OTHER
                          note = c is
                           8-Diethylamino-tricyclic-2'-deoxy-beta-D-ribonucleoside
source                    1..10
                          mol_type = other DNA
                          organism = synthetic construct
SEQUENCE: 11
cgcaccttcg                                                                 10

SEQ ID NO: 12             moltype = DNA  length = 10
FEATURE                   Location/Qualifiers
misc_feature              1..10
                          note = Synthetic DNA Oligonucleotide
modified_base             6
                          mod_base = OTHER
                          note = c is
                           8-Diethylamino-tricyclic-2'-deoxy-beta-D-ribonucleoside
source                    1..10
                          mol_type = other DNA
                          organism = synthetic construct
SEQUENCE: 12
cgcagcctcg                                                                 10

SEQ ID NO: 13             moltype = DNA  length = 10
FEATURE                   Location/Qualifiers
misc_feature              1..10
                          note = Synthetic DNA Oligonucleotide
modified_base             6
```

```
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 13
cgcaccatcg                                                                   10

SEQ ID NO: 14                 moltype = DNA   length = 10
FEATURE                       Location/Qualifiers
misc_feature                  1..10
                              note = Synthetic DNA Oligonucleotide
modified_base                 6
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 14
cgcagcgtcg                                                                   10

SEQ ID NO: 15                 moltype = DNA   length = 10
FEATURE                       Location/Qualifiers
misc_feature                  1..10
                              note = Synthetic DNA Oligonucleotide
modified_base                 6
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 15
cgcaccctcg                                                                   10

SEQ ID NO: 16                 moltype = DNA   length = 10
FEATURE                       Location/Qualifiers
misc_feature                  1..10
                              note = Synthetic DNA Oligonucleotide
modified_base                 6
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 16
cgcatcatcg                                                                   10

SEQ ID NO: 17                 moltype = DNA   length = 10
FEATURE                       Location/Qualifiers
misc_feature                  1..10
                              note = Synthetic DNA Oligonucleotide
modified_base                 6
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 17
cgcatcttcg                                                                   10

SEQ ID NO: 18                 moltype = DNA   length = 10
FEATURE                       Location/Qualifiers
misc_feature                  1..10
                              note = Synthetic DNA Oligonucleotide
modified_base                 6
                              mod_base = OTHER
                              note = c is
                              8-Diethylamino-tricyclic-2'-deoxy-beta-D-ribonucleoside
source                        1..10
                              mol_type = other DNA
                              organism = synthetic construct
SEQUENCE: 18
cgcaacatcg                                                                   10
```

```
SEQ ID NO: 19             moltype = DNA   length = 10
FEATURE                   Location/Qualifiers
misc_feature              1..10
                          note = Synthetic DNA Oligonucleotide
modified_base             6
                          mod_base = OTHER
                          note = c is tricyclic-2'-deoxy-beta-D-ribonucleoside
source                    1..10
                          mol_type = other DNA
                          organism = synthetic construct
SEQUENCE: 19
cgcaacatcg                                                              10

SEQ ID NO: 20             moltype = DNA   length = 10
FEATURE                   Location/Qualifiers
misc_feature              1..10
                          note = Synthetic DNA Oligonucleotide
source                    1..10
                          mol_type = other DNA
                          organism = synthetic construct
SEQUENCE: 20
cgatattgcg                                                              10

SEQ ID NO: 21             moltype = DNA   length = 10
FEATURE                   Location/Qualifiers
misc_feature              1..10
                          note = Synthetic DNA Oligonucleotide
modified_base             5
                          mod_base = OTHER
                          note = c is 1', 2'-dideoxyribose
source                    1..10
                          mol_type = other DNA
                          organism = synthetic construct
SEQUENCE: 21
cgatcttgcg                                                              10

SEQ ID NO: 22             moltype =    length =
SEQUENCE: 22
000

SEQ ID NO: 23             moltype =    length =
SEQUENCE: 23
000

SEQ ID NO: 24             moltype =    length =
SEQUENCE: 24
000

SEQ ID NO: 25             moltype =    length =
SEQUENCE: 25
000

SEQ ID NO: 26             moltype =    length =
SEQUENCE: 26
000

SEQ ID NO: 27             moltype =    length =
SEQUENCE: 27
000

SEQ ID NO: 28             moltype =    length =
SEQUENCE: 28
000

SEQ ID NO: 29             moltype =    length =
SEQUENCE: 29
000

SEQ ID NO: 30             moltype = DNA   length = 10
FEATURE                   Location/Qualifiers
misc_feature              1..10
                          note = Synthetic DNA Oligonucleotide
source                    1..10
                          mol_type = other DNA
                          organism = synthetic construct
SEQUENCE: 30
cgatgctgcg                                                              10

SEQ ID NO: 31             moltype = DNA   length = 10
```

```
FEATURE              Location/Qualifiers
misc_feature         1..10
                     note = Synthetic DNA Oligonucleotide
source               1..10
                     mol_type = other DNA
                     organism = synthetic construct
SEQUENCE: 31
cgaaggtgcg                                                              10

SEQ ID NO: 32        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 32
cgaggctgcg                                                              10

SEQ ID NO: 33        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 33
cgatggtgcg                                                              10

SEQ ID NO: 34        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 34
cgacgctgcg                                                              10

SEQ ID NO: 35        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 35
cgagggtgcg                                                              10

SEQ ID NO: 36        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 36
cgatgatgcg                                                              10

SEQ ID NO: 37        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 37
cgaagatgcg                                                              10

SEQ ID NO: 38        moltype = DNA   length = 10
FEATURE              Location/Qualifiers
misc_feature         1..10
                     note = Synthetic DNA Oligonucleotide
source               1..10
                     mol_type = other DNA
                     organism = synthetic construct
SEQUENCE: 38
cgatgttgcg                                                              10
```

```
SEQ ID NO: 39          moltype = DNA  length = 10
FEATURE                Location/Qualifiers
misc_feature           1..10
                       note = Synthetic DNA Oligonucleotide
source                 1..10
                       mol_type = other DNA
                       organism = synthetic construct
SEQUENCE: 39
cgatattgcg                                                            10

SEQ ID NO: 40          moltype = DNA  length = 10
FEATURE                Location/Qualifiers
misc_feature           1..10
                       note = Synthetic DNA Oligonucleotide
modified_base          5
                       mod_base = OTHER
                       note = c is 1', 2'-dideoxyribose
source                 1..10
                       mol_type = other DNA
                       organism = synthetic construct
SEQUENCE: 40
cgatcttgcg                                                            10

SEQ ID NO: 41          moltype = DNA  length = 10
FEATURE                Location/Qualifiers
misc_feature           1..10
                       note = Synthetic DNA Oligonucleotide
modified_base          6
                       mod_base = OTHER
                       note = c is
                       8-Diethylamino-tricyclic-2'-deoxy-beta-D-ribonucleoside
source                 1..10
                       mol_type = other DNA
                       organism = synthetic construct
SEQUENCE: 41
cgcaacatcg                                                            10
```

COMPOUNDS FOR FLUORESCENCE SENSING OF DUPLEX FORMATION

RELATED APPLICATIONS

This application is a continuation of U.S. application Ser. No. 16/346,708, filed May 1, 2019, which is a National Stage filing under 35 U.S.C. § 371 of International Application No. PCT/US2017/060776, filed Nov. 9, 2017, which claims priority under 35 U.S.C. § 119(e) to U.S. Provisional Patent Application No. 62/420,347 filed Nov. 10, 2016 and U.S. Provisional Patent Application No. 62/533,897 filed Jul. 18, 2017, which applications are incorporated herein by reference.

GOVERNMENT SUPPORT

This invention was made with government support under Grant No. 5R25GM058906 awarded by the National Institutes of Health. The government has certain rights in the invention.

SEQUENCE LISTING

The instant application contains a Sequence Listing which has been submitted electronically in ST.26 format and is hereby incorporated by reference in its entirety. The ST.26 copy, created on Jan. 17, 2024, is named 512.008US2_SL, and is 42,369 bytes in size.

BACKGROUND OF THE INVENTION

Since the recognition of 2-aminopurine's potential as a fluorescent adenine surrogate, the field has been driven by a desire to expand the capabilities of fluorescent nucleosides. Examples include Tor's isomorphic RNA alphabet (*J. Am. Chem. Soc.* 2015, 137, 14602), Wilhelmsson's (*Nucleic Acids Res.* 2016, 44, e101) inter-nucleobase FRET pair, Sasaki's (*Tetrahedron* 2011, 67, 6746) fluorescent sensors for nucleobase damage, and nucleobase surrogates that can report on events in the major groove, such as protein binding. However, most fluorescent nucleobase analogues are quenched when base stacked, emit only at wavelengths <525 nm, and many perturb duplex structure.

Additionally, nucleoside analogues with substantial fluorescent turn-on responses upon incorporation have not yet been reported. The closest is Luedtke's $^{DMA}T$ nucleoside, which exhibits up to seven-fold increase in quantum yield when base-paired with A, but this analogue is fluorescent as a free nucleoside ($\Phi_{em}$=0.03) and the mechanism of its fluorescence increase was not studied in detail (*Chem. Commun.* 2016, 52, 4718).

Very little progress has been made towards developing nucleoside analogues that markedly increase their fluorescence upon duplex formation. Accordingly, a nucleoside analogue that is virtually non-fluorescent as a free nucleoside but becomes much brighter when base stacked has great value in turn-on fluorescence sensing applications for both enzymatic DNA and/or RNA synthesis and strand hybridization.

SUMMARY

Herein is disclosed the design and synthesis of new tricyclic cytidine compounds, for example, 8-diethylamino-tC (8-DEA-tC), that respond to DNA and/or RNA duplex formation with up to a 20-fold increase in fluorescent quantum yield as compared with the free nucleoside, depending on neighboring bases (FIG. 7). This turn-on response to duplex formation is greater than any reported nucleoside analogue that can participate in Watson-Crick base pairing. Measurements of the quantum yield of 8-DEA-tC mispaired with adenosine and, separately, opposite an abasic site show that there is almost no fluorescence increase without the formation of correct Watson-Crick hydrogen bonds. Kinetic isotope effects from the use of deuterated buffer show that the duplex protects 8-DEA-tC against quenching by excited state proton transfer. These results, supported by DFT calculations, provide a rationale for the observed photophysical properties that is dependent on duplex integrity and the electronic structure of the analogue.

Accordingly, this disclosure provides a compound of Formula I:

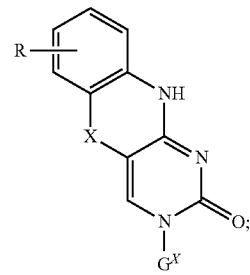

(I)

wherein

R is $OR^1$, or $NR^2R^3$, wherein R is at the ortho, meta, meta', or para position relative to the NH substituent of Formula I;

X is O, C=O, $NR^4$, S, S=O, or $S(=O)_2$;

$G^x$ is a moiety of Formula X1 or X2;

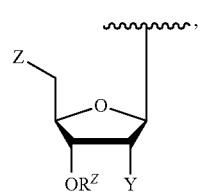

(X1)

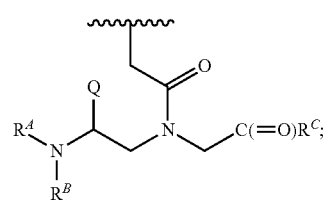

(X2)

Y is H, OH, halo, or Me;

Z is OH, O(dimethoxytrityl), guanidinium, phosphate, diphosphate, triphosphate, phosphoramidite, phosphorothioate, or —O$_2$P(=O)(3'-X1A) wherein Formula X1A is,

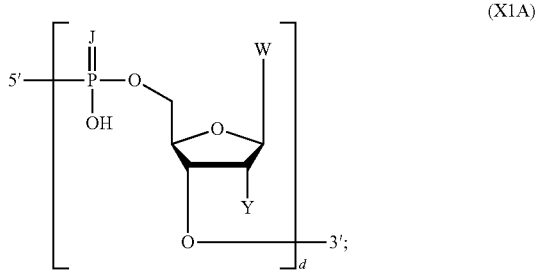

$R^Z$ is H, —P(N(R$^4$)$_2$)(OCH$_2$CH$_2$CN), or —O$_2$P(=O)(5'-X1A);

$R^1$, $R^2$, and $R^3$ are each independently CH$_3$, CH$_2$CH$_3$, or (C$_3$-C$_{12}$)alkyl wherein alkyl is optionally branched;

$R^4$ is H, CH$_3$, or CH$_2$CH$_3$, CH(CH$_3$)$_2$;

each Q is independently H, CH$_3$, CH$_2$CH$_3$, (C$_3$-C$_{12}$)alkyl wherein alkyl is optionally branched, or —(CH$_2$CH$_2$O)$_n$(C$_1$-C$_4$)alkyl where n is 1-20, and when Q is not H the carbon of the CH—Q bond is a stereocenter having an (R)-configuration, or an (9-configuration;

$R^A$ is H, CH$_3$, CH$_2$CH$_3$, (C$_3$-C$_{12}$)alkyl wherein alkyl is optionally branched, or an amide bond to X2A wherein Formula X2A is,

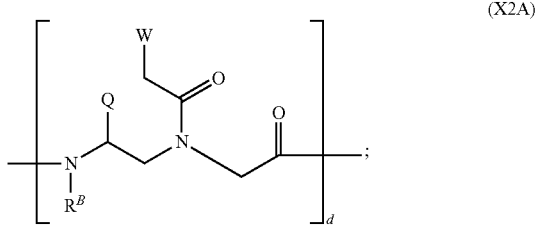

$R^B$ is H, CH$_3$, CH$_2$CH$_3$, (C$_3$-C$_{12}$)alkyl wherein alkyl is optionally branched, or a protecting group;

$R^C$ is OH, OCH$_3$, OCH$_2$CH$_3$, O(C$_3$-C$_{12}$)alkyl wherein alkyl is optionally branched, or an amide bond to X2A;

each J is independently 0 or S, and when J is S the phosphorous stereocenter has an (R)-configuration, or an (S)-configuration;

each W is independently adenine (A), thymine (T), cytosine (C), guanine (G), or Formula IA, wherein Formula IA is,

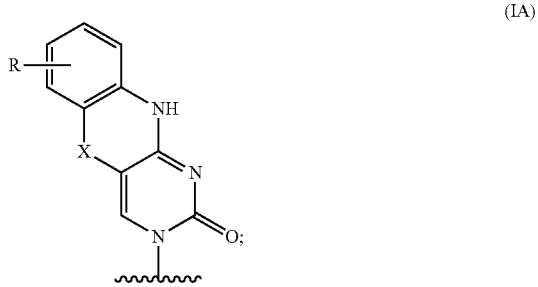

and d is 1 to about 50.

The disclosure also provides a phosphoramidite compound 2 as shown below:

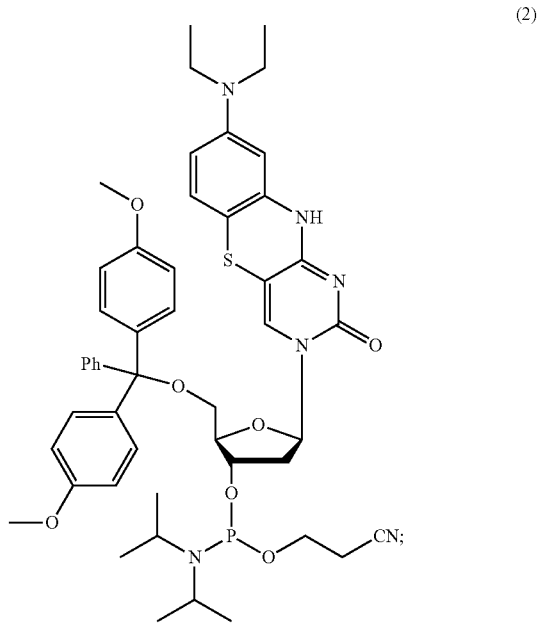

or a salt, solvate, or derivative thereof. Useful derivatives include other lengths of the alkyl groups and/or alkoxy groups on the compound (e.g., (C$_1$-C$_{10}$)alkyl, straight chain, branched, or cyclic, and/or (C$_1$-C$_{10}$)alkoxy, straight chain, branched, or cyclic). Compound 2 and its derivatives can also be modified to provide a nucleoside triphosphate. The triphosphate can be useful for enzymatic DNA or RNA synthesis and for detecting amplified nucleic acids such as DNA or RNA.

The invention further provides a method of detecting DNA duplex formation comprising:
  a) combining a compound of Formula I, which is incorporated into an oligonucleotide, and a sample comprising DNA or RNA in a solvent to form a mixture;
  b) detecting a fluorescent signal from the mixture;
  c) quantifying the signal, for example, by calculating a quantum yield or visualizing an increase in the brightness of fluorescence; and
  d) comparing the quantum yield or brightness increase to a control sample wherein the control sample is a compound of Formula I, thereby determining the presence or absence of double-stranded DNA or RNA.

Furthermore, this disclosure provides a method of differentiating nucleic acid sequences, the method comprising:
  a) incorporating a compound of claim 1 into a sample comprising DNA or RNA wherein the compound is a DNA or RNA probe of Formula I or a peptide nucleic acid (PNA) probe of Formula I, wherein $R^A$ and $R^C$ are X2A, and the DNA, RNA, or PNA probe has specific sequence that is complementary to the DNA or RNA sample;
  b) detecting a fluorescent signal, wherein the signal is optionally detected by fluorescence microscopy;
  c) quantifying the signal, wherein duplex formation of the PNA probe with the DNA or RNA provides an increase in fluorescence when the tricyclic cytosine moiety of the PNA probe is based-paired with moiety G of the DNA or RNA; and d) identifying differentiated DNA or RNA sequences;
wherein duplex formation of the DNA, RNA, or PNA probe with the complementary sequence of DNA or RNA differentiates the complementary nucleic acid sequence of DNA or RNA from a non-complementary sequence of DNA or RNA.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
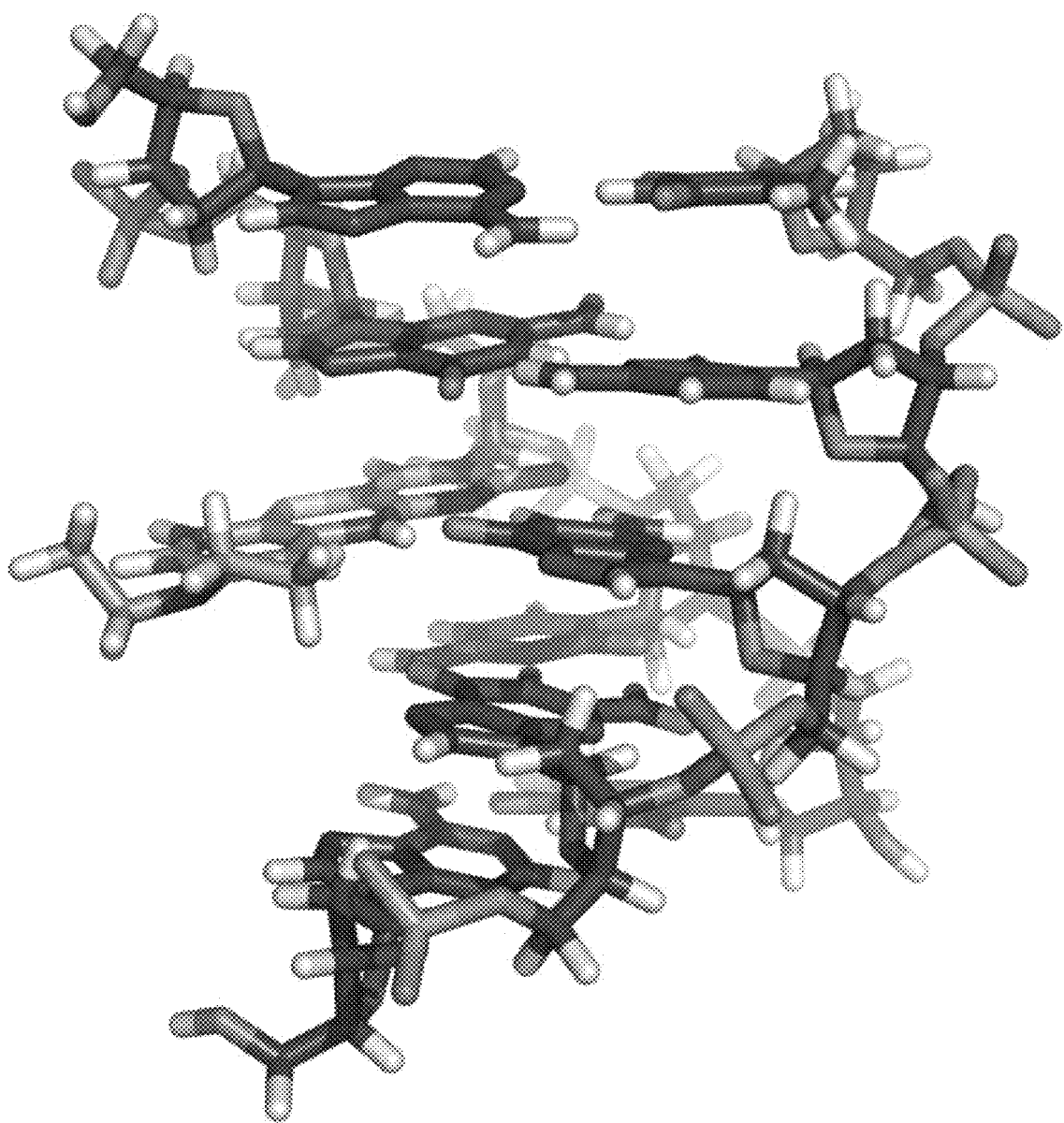
FIG. 1. 8-DEA-tC in the sequence 5'-AG(8-DEA-tC)CT-3' hybridized to its complement. The 8-DEA-tC molecule (orange C atoms) protrudes into the major groove where there is ample space for the diethylamino group to rotate freely. Molecular model prepared using Spartan '08 with the default structural parameters for B form DNA. The native atoms of the natural DNA were held frozen and the geometry of the additional atoms of the 8-DEA-tC nucleobase was optimized using molecular mechanics and the MMFF force field.

Based on prior experience with tricyclic cytidines (tC molecules), a hypothesis was formulated that electronic modification of tC to favor a charge-separated excited state would unlock a fluorescence turn-on response to duplex formation. Herein disclosed is a novel tricyclic cytidine analogue 8-DEA-tC, 1 (see Formula A) that exhibits up to a 20-fold fluorescence enhancement in duplex DNA as compared with its almost non-fluorescent free nucleoside ($\Phi_{em}$=0.006). Provided herein is the first mechanistic relationships between structure and this type of fluorescence turn-on response. Formula A shows 8-DEA-tC and parent tC nucleosides with Watson-Crick base pairing with G.

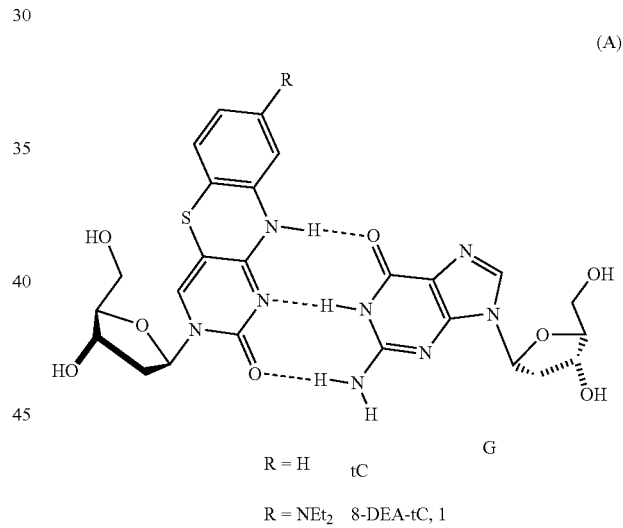

(A)

The invention provides various modifications to cytidine—one of the four building blocks of natural DNA (the C of A, T, C, G). Certain modifications cause the modified cytidine to become fluorescent upon incorporation into the DNA strand, particularly in matched, double-stranded DNA. This property is useful because it enables fluorescent detection of DNA synthesis. Current methods for detecting DNA synthesis by fluorescence use dyes that bind to the DNA in a process called intercalation. These dyes become fluorescent when intercalated. The advantage of using a cytidine modification is that our fluorescence turn-on response is sequence-specific, whereas the intercalating dyes bind to any double-stranded DNA. Another property of the new compounds, such as the 8-DEA-tC molecule, in DNA is that the fluorescence is enhanced when the two DNA strands bind together to form the double helix, and this fluorescence enhancement depends on sequence. The fluorescence properties have been studied and characterized.

Another application, for example, with DNA or RNA, is to use a compound described herein to detect specific sequences of genetic material. The method can be used to differentiate between strains of bacteria using oligonucleotides that contain 8-DEA-tC. This can provide an inexpensive and robust method to differentiate microorganisms and/or viruses. The compounds can also be useful, for example, in biophysics applications, such as the use of our 8-DEA-tC molecule, or a derivative thereof, in qPCR, the detection of RNA folding, and the monitoring of DNA synthesis, ideally in a living cell. The application in RNA folding may make the molecule useful for drug screening against RNA targets, which include new possibilities to overcome antibiotic resistance.

Another important component of research involves peptide nucleic acids (PNAs), which are synthetic molecules that feature the natural hydrogen bonding bases found in DNA (G, A, C and T) attached to an unnatural peptide-like backbone (Scheme A), wherein "Base" is a moiety of Formula I as described herein, and each set of parentheses in Scheme A indicate "n" repeating units, where n is 1 to about 5, or 1 to about 10, or 1 to about 100, 10 to about 100, or about 50 to about 500. For example, in Formula I, the nitrogen atom of $R^A$ or $R^B$ can be conjugated to another X2 moiety of another Formula I molecule via an amide bond at the $CO_2R^C$ moiety such that $R^A$ or $R^B$, and $R^C$, are a bond, forming an amide bond, thereby forming a dimer, or oligomer if additional $R^A$ or $R^B$, and $R^C$ form bonds, wherein the oligomer has the number of repeating units "n" as described above.

The bases are spaced apart by approximately the same distance as in DNA or RNA, allowing PNA to hybridize to complementary DNA or RNA targets by the standard Watson-Crick rules of base pairing. The lack of a negative charge on the PNA backbone allows complementary PNA and DNA (or RNA) strands to form more stable double helices than corresponding DNA-DNA, DNA-RNA or RNA-RNA partners, meaning PNA exhibits high affinity for its targets. This raises the possibility of using PNA to interfere with gene expression, based on the hypothesis that strong binding of PNA to an intracellular DNA or RNA target will prevent transcription, splicing, translation or other essential steps in the process by which genetic information is converted into a functional RNA or protein molecule. The unnatural backbone of PNA is also favorable for biological applications, since it is sufficiently distinct from both protein and nucleic acid structures as to be inert toward both protease and nuclease enzymes.

Scheme A. Peptide nucleic acids (PNAs).

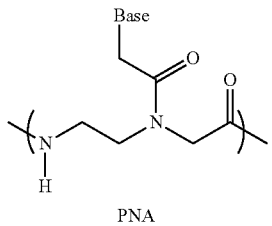

PNA

-continued

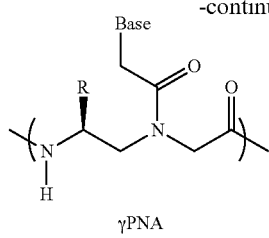

γPNA

Fluorescence is used as a primary tool in biophysics to study the properties of the molecules that make up our cells, and how problems in the operation or information content of these molecules lead to diseases. For these applications, a fluorescence turn-on response is preferred over a turn-off response because of greater sensitivity and because quenching—a process where other molecules turn off fluorescence—can cause false positives in fluorescence turn-off sensors. Disclosed herein is a way to use synthetic chemistry to modify the structure of cytidine, the C of the genetic code, to enable it to serve as a fluorescence turn-on sensor for the formation of the DNA and/or RNA duplex while causing only slight perturbations to the natural structure. Our new tool is useful for visualizing DNA and/or RNA synthesis and discriminating between matched and mismatched DNA and/or RNA sequences.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "peptide nucleic acid" (PNA) refers to an artificially synthesized polymer similar to DNA or RNA. Synthetic peptide nucleic acid oligomers have been used in molecular biology procedures, diagnostic assays, and antisense therapies. Due to their higher binding strength, it is possible to use shorter PNA oligomers in these roles, usually requiring oligonucleotide probes of about 20-25 bases. The main concern of the length of the PNA-oligomers is the specificity. PNA oligomers also show greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to degradation by enzymes. PNAs are also stable over a wide pH range. Since the backbone of PNA contains no charged phosphate groups, the binding between PNA/DNA strands is stronger than between DNA/DNA strands due to the lack of electrostatic repulsion. However, this also causes it to be hydrophobic. In this disclosure, PNAs can be chemically modified to improve solubility through a covalently attached solubilizing functional group, for example, a polyethylene glycol (PEG) moiety.

The term "polyethylene glycol" (PEG) refers to an oligomer or polymer of ethylene oxide. PEGs are prepared by polymerization of ethylene oxide and are commercially available over a wide range of molecular weights from 300 g/mol to 10,000,000 g/mol. PEGs of different molecular weights find use in different applications, and have different physical properties (e.g. viscosity) due to chain length effects.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "amino" refers to —$NH_2$. The amino group can be optionally substituted as defined herein for the term "substituted".

The term "substituted" refers to an organic group in which one or more bonds to a hydrogen atom contained therein are replaced by one or more bonds to a non-hydrogen atom such as, but not limited to, an alkyl, an aryl, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R)$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O) OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

The term "masking group" is similar to the term "protecting group" in that it refers to those groups intended to protect a functional group such as, but not limited to OH, NH$_2$, COOH against undesirable reactions during synthetic procedures or contact with enzymes or metabolic processes, and which can later be removed to reveal the functional group. Commonly used protecting groups, for example, are disclosed in Protective Groups in Organic Synthesis, Greene, T. W.; Wuts, P. G. M., John Wiley & Sons, New York, N.Y. However, the masking group as defined herein refer to only those types of protecting groups that can be removed by a specific enzyme or metabolic process inside a cell or certain compartment within a cell.

The terms "ortho", "meta", "meta'", and "para", are defined in this disclosure for Formula I and Formula II as shown in Formula X:

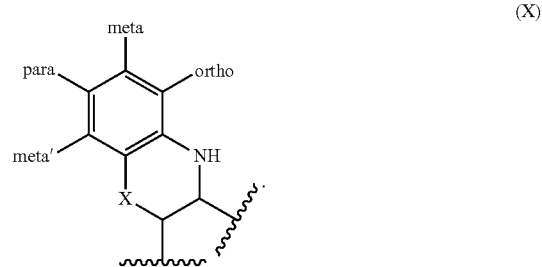

(X)

Embodiments of the Invention

This disclosure provides various embodiments of a compound of Formula I:

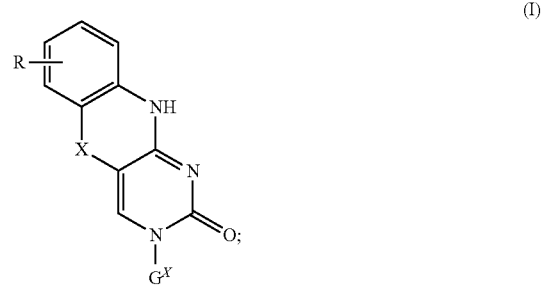

(I)

wherein

R is OR$^1$, or NR$^2$R$^3$, wherein R is at the ortho, meta, meta', or para position relative to the NH substituent of Formula I;

X is O, C=O, NR$^4$, S, S=O, or S(=O)$_2$;

G$^x$ is a moiety of Formula X1 or X2;

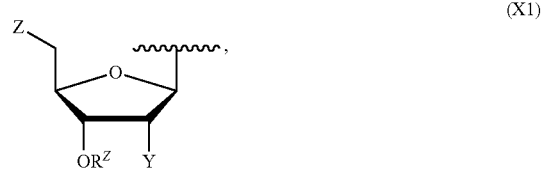

(X1)

-continued

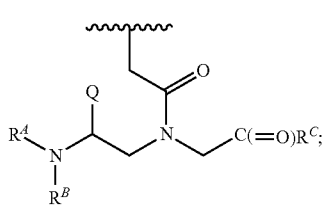
(X2)

Y is H, OH, halo, or Me;

Z is OH, O(dimethoxytrityl), guanidinium, phosphate, diphosphate, triphosphate, phosphoramidite, phosphorothioate, or —O$_2$P(=O)(3'-X1A) wherein Formula X1A is,

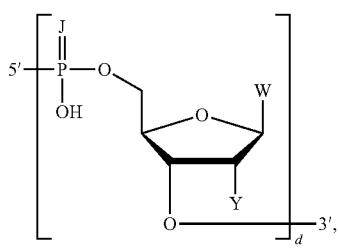
(X1A)

wherein the phosphate moiety is covalently bonded to the 3'-position of Formula X1A as shown;

$R^Z$ is H, —P(N($R^4$)$_2$)(OCH$_2$CH$_2$CN), or —O$_2$P(=O)(5'-X1A), wherein the phosphate moiety is covalently bonded to the 5'-position of Formula X1A as shown;

$R^1$, $R^2$, and $R^3$ are each independently CH$_3$, CH$_2$CH$_3$, or (C$_3$-C$_{12}$)alkyl wherein alkyl is optionally branched;

$R^4$ is H, CH$_3$, or CH$_2$CH$_3$, CH(CH$_3$)$_2$;

each Q is independently H, CH$_3$, CH$_2$CH$_3$, (C$_3$-C$_{12}$)alkyl wherein alkyl is optionally branched, or —(CH$_2$CH$_2$O)$_n$(C$_1$-C$_4$)alkyl where n is 1-20, and when Q is not H the carbon of the CH—Q bond is a stereocenter having an (R)-configuration, or an (S)-configuration;

$R^A$ is H, CH$_3$, CH$_2$CH$_3$, (C$_3$-C$_{12}$)alkyl wherein alkyl is optionally branched, or an amide bond to X2A wherein Formula X2A is,

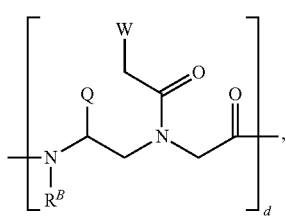
(X2A)

wherein $R^A$ is a bond to the carbonyl moiety on the shown right side of Formula X2A;

$R^B$ is H, CH$_3$, CH$_2$CH$_3$, (C$_3$-C$_{12}$)alkyl wherein alkyl is optionally branched, or a protecting group;

$R^C$ is OH, OCH$_3$, OCH$_2$CH$_3$, O(C$_3$-C$_{12}$)alkyl wherein alkyl is optionally branched, or an amide bond to X2A, wherein $R^C$ is a bond to the amino moiety on the shown left side of Formula X2A;

each J is independently O or S, and when J is S the phosphorous stereocenter has an (R)-configuration, or an (S)-configuration;

each W is independently adenine (A), thymine (T), cytosine (C), guanine (G), or Formula IA, wherein Formula IA is,

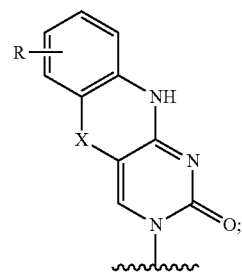
(IA)

and d is 1 to about 50. In other various embodiments in this disclsoure, d is 1 to about 100, d is 1 to about 75, 1 to about 40, 1 to about 30, 1 to about 25, 1 to about 20, 1 to about 15, 1 to about 10, 1 to about 5, less than about 10, less than about 9, less than about 8, less than about 6, less than about 5, less than about 4, or less than about 3.

In some embodiments, R is meta-N(CH$_2$CH$_3$)$_2$, X is S, and Formula IA is moiety IB, wherein moiety IB is,

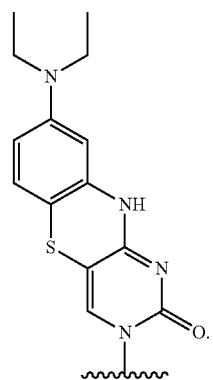
(IB)

This disclosure also provides embodiments of compounds of Formula I that are compounds of Formula II:

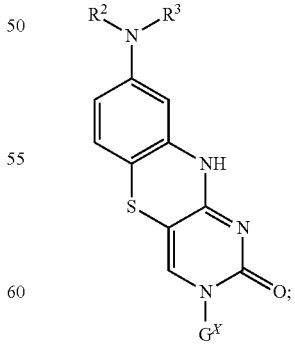
(II)

wherein

Y is H, OH, F, Cl, or Me;

Z is OH, O(dimethoxytrityl), phosphate, triphosphate, or —O$_2$P(=O)(3'-X1A);

$R^Z$ is H, —P(N(CH(CH$_3$)$_2$)$_2$)(OCH$_2$CH$_2$CN), or —O$_2$P(=O)(5'-X1A);

$R^2$, and $R^3$ are each independently CH$_3$, CH$_2$CH$_3$, propyl, isopropyl, or cyclopropyl;

Q is H, CH$_3$, CH$_2$CH$_3$, CH$_2$CH$_2$CH$_3$, or CH(CH$_3$)$_2$;

$R^A$ is H, CH$_3$, CH$_2$CH$_3$, CH$_2$CH$_2$CH$_3$, CH(CH$_3$)$_2$, or an amide bond to X2A;

$R^C$ is OH, OCH$_3$, OCH$_2$CH$_3$, or an amide bond to X2A; and d is 1-20.

In additional embodiments, the substituent Z is a phosphate, phosphite, diphosphate, triphosphate, phosphoramidite, phosphonite, phosphonate, phosphinite, phosphinate, phosphine, phosphine oxide, phosphoramidate, phosphorodiamidite, phosphorodiamidate, phosphoramide, phosphonamidate, phosphonamide, phosphinamide, phosphorothioite, phosphorothioate, phosphorodithioite, or phosphorodithioate.

In various embodiments of Formula I and Formula II, R is Br, Cl, F, CN, NO$_2$, OR$^1$, or NR$^2$R$^3$. In other embodiments, R$^1$ is methyl. In yet other embodiments, R$^2$ and R$^3$ are each methyl or ethyl. In some additional embodiments, the substituent R is ortho, meta, or para to the substituent X. In some other embodiments, the substituent R is ortho, meta, or para to the NH substituent. In some additional embodiments, R is Cl, CN, OR$^1$, or NR$^2$R$^3$; and X is O, or S. In some various embodiments, X is O or S. In yet some other embodiments, R is N(CH$_2$CH$_3$)$_2$, and X is S.

In various additional embodiments of Formula I and Formula II, Q is H, CH$_3$, CH$_2$CH$_3$, CH$_2$CH$_2$CH$_3$, CH(CH$_3$)$_2$, or —(CH$_2$CH$_2$O)$_n$(C$_1$-C$_4$)alkyl, where n is 1-20. In other various embodiments, R$^B$ is H, and R$^A$ is H, CH$_3$, CH$_2$CH$_3$, CH$_2$CH$_2$CH$_3$, CH(CH$_3$)$_2$, tert-butyloxycarbonyl (Boc), or conjugated to another X2 moiety via an amide bond at the CO$_2$R$^C$ moiety. In some embodiments, when Q is not H the carbon of the CH—Q bond is a stereocenter having an (R)-configuration. In some other embodiments, when Q is not H the carbon of the CH—Q bond is a stereocenter having an (S-configuration.

In various other embodiments of Formula I and Formula II, the substituent R is NR$^2$R$^3$. In other embodiments, R$^2$ and R$^3$ are each independently methyl, ethyl, propyl, isopropyl, cyclopropyl. In yet other embodiments, the substituent R is meta, meta', or para to the NH substituent of Formula I. In additional embodiments, R is NR$^2$R$^3$; and X is O, or S. In yet other embodiments, X is S.

This disclosure provides additional embodiments of compounds of Formula I and Formula II, wherein the compound is 8-DEA-tC, compound 2, a compound of Formula X3, or a compound of Formula X4:

(2)

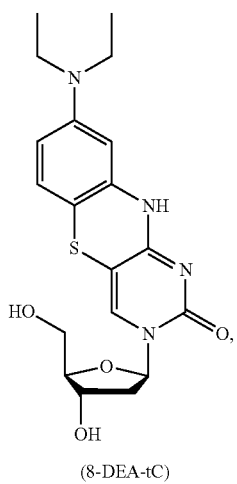

(8-DEA-tC)

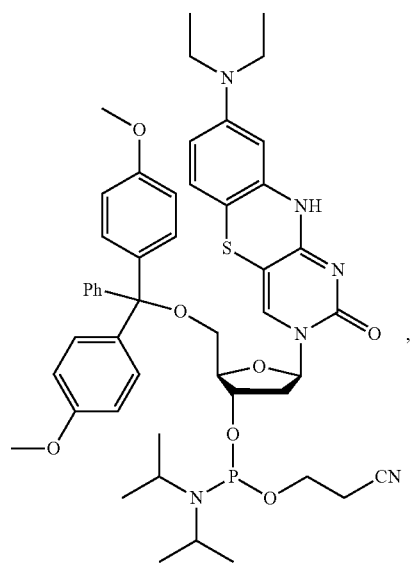

-continued
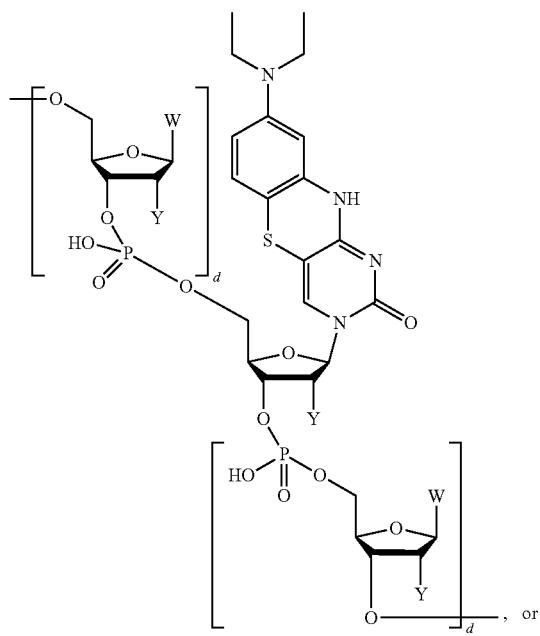
(X3)
, or
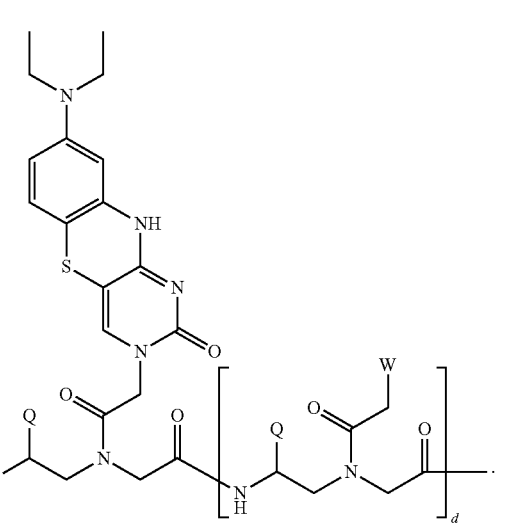
(X4)

Furthermore, this disclosure provides other embodiments of compounds of Formula I and Formula II that are compounds of Formula III:

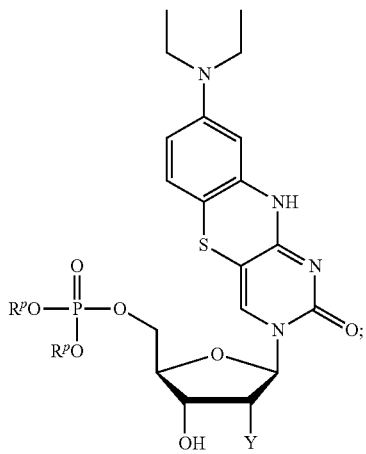

(III)

wherein

Y is H or OH; and each $R^P$ is independently H, phosphate, diphosphate, alkyl, aryl, or a masking group, wherein the masking group is hydrolysable by cytoplasmic esterases inside a cell; and optionally each $OR^P$ is independently an amino moiety.

This disclosure provides additional embodiments of compounds of Formula III, wherein the compound is a compound of Formula X5, a compound of Formula X6, or a compound of Formula X7:

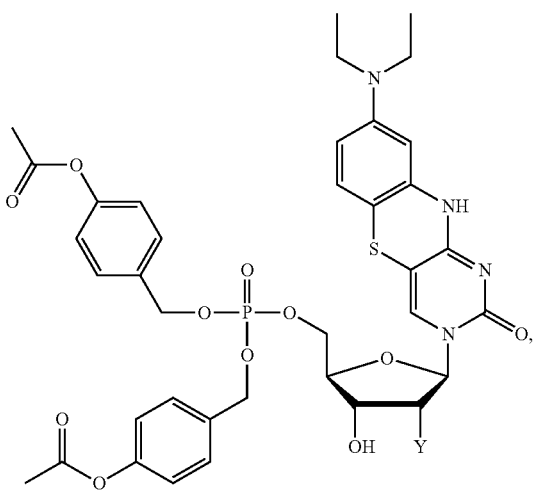

(X5)

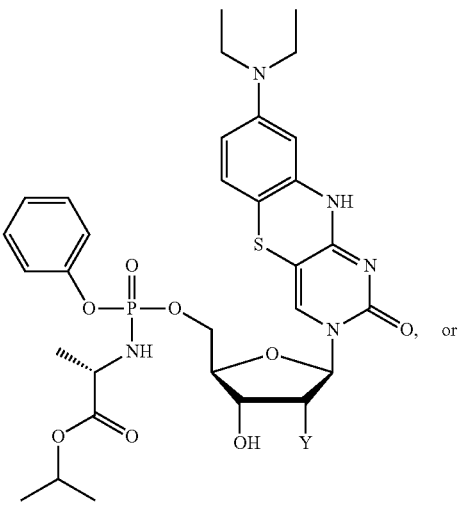

(X6)

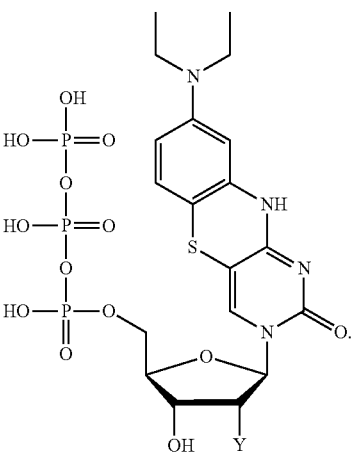

(X7)

In addition, the disclosure provides novel compounds of Formula I, Formula II and Formula III, intermediates for the synthesis of compounds of Formula I, Formula II and Formula III, as well as methods of preparing compounds of Formula I, Formula II and Formula III. The invention also provides compounds of Formula I, Formula II and Formula III that are useful as intermediates for the synthesis of other useful compounds.

The disclosure also provides a method to probe enzymatic DNA synthesis by use of a phosphoramidite compound, such as a compound of Formula II, e.g., compound 2, the steps comprising: a) combining the compound of Formula II with a sample of DNA; b) detecting a fluorescent signal from the sample; c) quantifying the signal by calculating a quantum yield; and d) comparing the quantum yield to a control sample.

This disclosure also provides a method of quantifying nucleic acid synthesis in a cell, the method comprising:

a) incorporating a compound of claim 1 into the DNA or RNA of a cell, wherein the compound is optionally introduced into a cell by transfecting the cell with a plasmid encoding a nucleotide transporter protein, for example, *Phaeodactylum tricornutum* (PtNTT2) and *Thalassiosira pseudonana* (TpNTT2), wherein the compound of claim 1 is a compound that comprises a nucleoside triphosphate;

b) optionally exposing the cell to a chemical transfection agent, or applying electroporation, wherein the compound of claim 1 is a compound that comprises a nucleoside triphosphate;
c) detecting a fluorescent signal during nascent DNA or RNA synthesis, wherein the signal is optionally detected by fluorescence microscopy;
d) quantifying the signal, wherein duplex formation of the compound with the DNA or RNA of the cell provides an increase in fluorescence when the tricyclic cytosine moiety of the compound is based-paired with moiety G in the nucleic acids of the cell; and
e) assessing cell parameters, wherein the cell parameters comprise cytotoxicity, cell permeability, viral replication, metabolic activity, DNA synthesis, transcription rates, kinetics, rate constants, half-life, or a combination thereof;
wherein said cell parameters are assessed by quantifying the nucleic acid synthesis in a cell.

Additionally, the disclosure provides a method of differentiating nucleic acid sequences, the method comprising:
a) incorporating a compound of claim 1 into a sample comprising DNA or RNA wherein the compound is a DNA probe or RNA probe of Formula I wherein Z is —O$_2$P(=O)(3'-X1A) and R$^Z$ is —O$_2$P(=O)(5'-X1A), or wherein the compound is peptide nucleic acid (PNA) probe of Formula I wherein R$^A$ is X2A and R$^C$ is X2A, and the DNA, RNA or PNA probe has a specific sequence that is complementary to the sample DNA or RNA;
b) detecting a fluorescent signal, wherein the signal is optionally detected by fluorescence microscopy;
c) quantifying the signal, wherein duplex formation of the DNA, RNA, or PNA probe with the sample DNA or RNA provides an increase in fluorescence when the tricyclic cytosine moiety of the DNA, RNA, or PNA probe is based-paired with moiety G of the sample DNA or RNA; and
d) identifying differentiated DNA or RNA sequences in the sample;
wherein duplex formation of the DNA, RNA, or PNA probe with a complementary sequence of sample DNA or RNA differentiates the complementary nucleic acid sequence of sample DNA or RNA from a non-complementary sequence of sample DNA or RNA.

Furthermore, the disclosure provides a method of quantifying the progression of a polymerase chain reaction (PCR), the method comprising:
a) incorporating a compound of claim 1 into a DNA or RNA primer for a PCR reaction, replacing natural (d)CTP (deoxycytidine triphosphate) with a compound of claim 1 in the PCR reaction, or a combination thereof, wherein DNA or RNA is amplified;
b) detecting a fluorescent signal;
c) quantifying the signal, wherein duplex formation of the compound with the DNA or RNA provides an increase in fluorescence when the tricyclic cytosine moiety of the compound is based-paired with moiety G of the DNA or RNA; and
d) tracking the amplified RNA or DNA;
wherein the progression of the PCR is quantified.

Various embodiments of this disclosure provide a method of detecting nucleic acids, the method a) combining a compound of claim 1 that has been incorporated into an oligonucleotide, and a sample comprising DNA or RNA in a solvent to form a mixture;

b) detecting a fluorescent signal from the mixture, wherein the signal is optionally detected by fluorescence microscopy;
c) quantifying the signal, wherein duplex formation of the compound with the DNA or RNA provides an increase in fluorescence when the tricyclic cytosine moiety of the compound is based-paired with moiety G of the DNA or RNA; and
d) comparing the quantum yield to a control sample wherein the control sample comprises the compound of claim 1;
wherein the presence or absence of double-stranded DNA or RNA is determined.

In various embodiments of the disclosed methods, the solvent comprises an aqueous buffer. The aqueous buffer can be any aqueous buffer that allows double-stranded DNA to be stable. In other embodiments, the solvent comprises an aqueous 1×PBS buffer. In some additional embodiments, the solvent comprises an aqueous 0.5×PBS buffer. In some other embodiments, the solvent comprises 1,4-dioxane.

In various additional embodiments of the disclosed methods, the quantifying the signal comprises measuring or calculating a quantum yield, or visualizing an increase in the brightness of fluorescence.

Fluorescence Turn-on Sensing of DNA Duplex Formation by a Tricyclic Cytidine Analogue Disclosed herein is the design and synthesis of a novel tricyclic cytidine analogue, 8-DEA-tC, that is almost non-fluorescent as a nucleoside but exhibits up to a 20-fold increase in $\Phi_{em}$ when base stacked in duplex DNA. A synthesis of 8-DEA-tc nucleoside (1) is represented by Scheme 1.

This is the first nucleoside analogue to match the performance of ethidium bromide at fluorescence turn-on detection of DNA duplex formation, but it offers the distinct advantage of sequence-specificity. Studies of 8-DEA-tC mismatched with adenosine or positioned across from an abasic site reveal that correct Watson-Crick base pairing is essential to the fluorescence turn-on response, at least in part because base pairing protects 8-DEA-tC from quenching by excited state proton transfer involving the solvent.

The synthesis of 8-DEA-tC 1 was developed based on previous syntheses of tC derivatives (*Chem. Eur. J.* 2014, 20, 2010). Doubly alkylating 5-amino-2-methylbenzothiazole 2 with bromoethane was initially performed. Next, a nucleophilic opening of the thiazole ring was done using hydrazine to afford 4-diethylamino-2-aminothiophenol, which oxidized under air to give the disulfide 3 (64% over two steps). Then, the disulfide was reduced using triethylphosphine followed by a substitution reaction with 5-bromouracil in one pot to yield thioether 4 (36%). Heating this compound at 120° C. in a mixture of concentrated HCl and butanol effected ring closure to afford the 8-DEA-tC nucleobase 5 (97%). Activation of 5 using BSA to give the TMS ether and ribosylation in the same pot using Hoffer's chlorosugar 6 resulted in a 1:1 mixture of the α and β anomers in a combined yield of 86%. Isolation of the β anomer was facilitated by the removal of the toluoyl groups to give the 8-DEA-tC nucleoside 1. Standard procedures were used for dimethoxytrityl protection and phosphoramidite preparation to ready the nucleoside for solid-phase DNA synthesis (see Examples section below).

Scheme 1. Synthesis of 8-DEA-tC nucleoside 1.

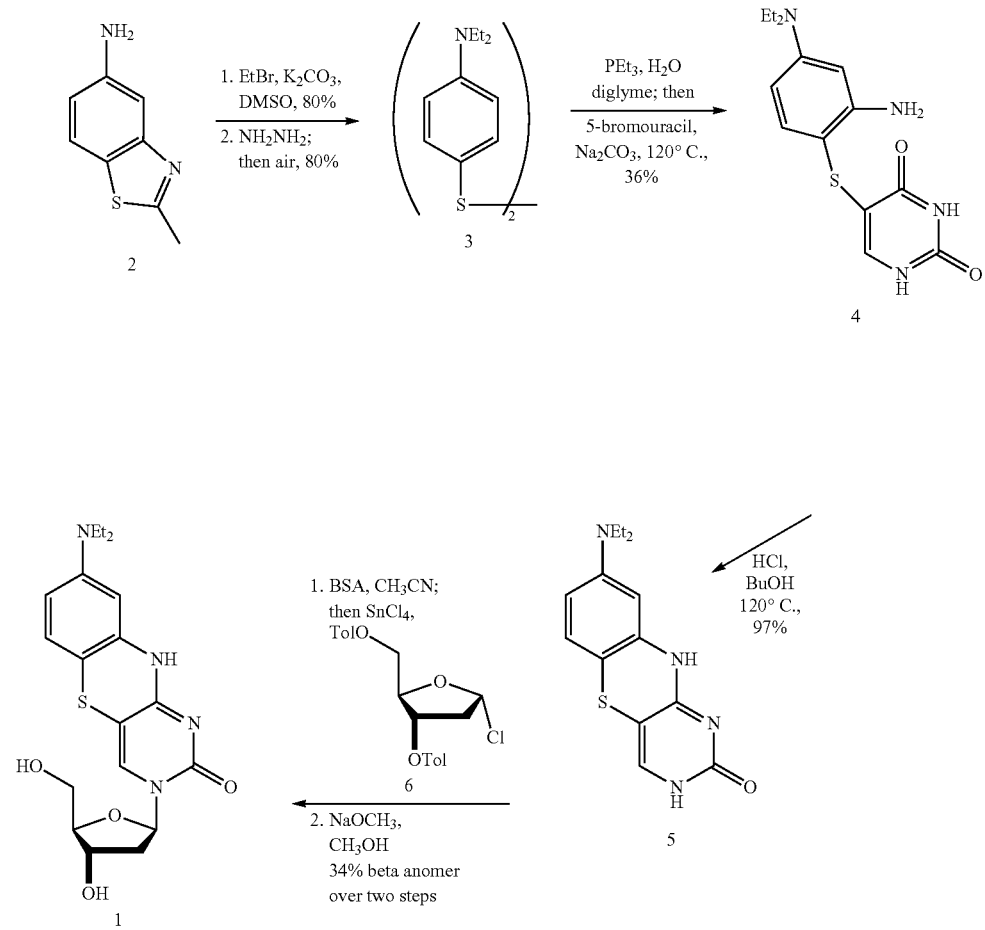

Photophysical measurements of the 8-DEA-tC nucleoside revealed $\varepsilon=2700$ M$^{-1}$ cm$^{-1}$, $\lambda_{max,abs}=395$ nm, $\Delta_{max,em}=493$ nm a $\Phi_{em}=0.006$ in 1x PBS buffer. Because protic solvents often quench organic fluorophores, similar measurements were made in 1,4-dioxane and it was observed that $\lambda_{max,abs}=389$ nm, $\lambda_{max,em}=524$ nm, and $\Phi_{em}=0.06$, a 10-fold increase. This increase is larger than that of the parent tC for the same solvent change (4-fold) but smaller than what was observed for 8-methoxy-tC nucleoside (30-fold).

To test the properties of 8-DEA-tC in single-stranded and duplex oligonucleotides, the nucleoside phosphoramidite was used in solid-phase DNA synthesis to prepare 9 decameric oligos along with complementary sequences, a mismatch, or dSpacer (1',2'-dideoxyribose) as stable abasic site surrogate were also prepared. To study the impact of the 8-DEA-tC modification on tertiary structure, all sequences were annealed to their complements, and analyzed using circular dichroism (see Examples section below). All spectra are consistent with B form helices, indicating that 8-DEA-tC does not significantly perturb the tertiary structure.

Figure 2:
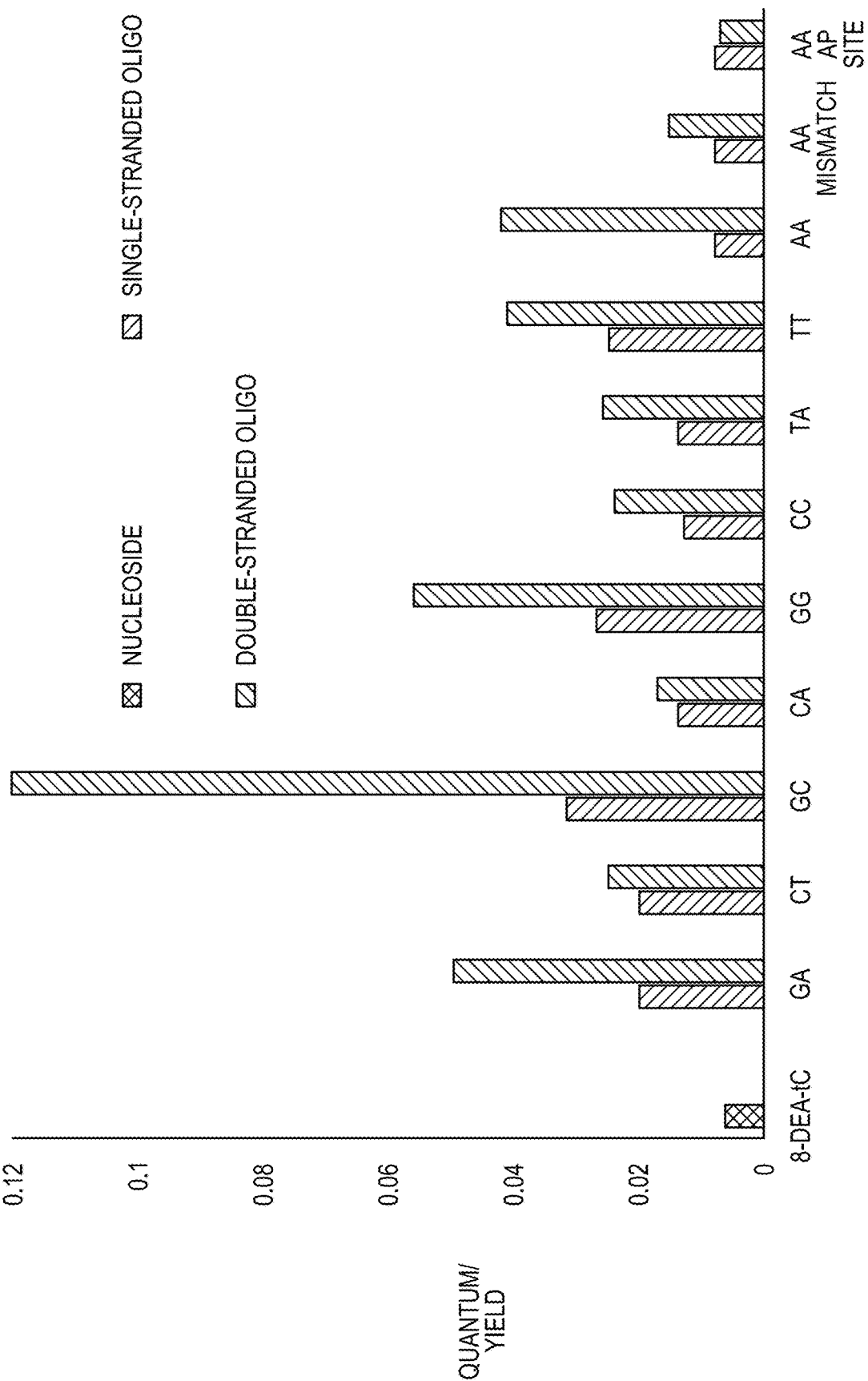
FIG. 2. Quantum yields of the 8-DEA-tC nucleoside in single-stranded and double-stranded oligonucleotides (For sequences provided in Table 1).

Quantum yields of fluorescence emission were determined using the comparative method of Williams et. al. (*Analyst* 1983, 108, 1067) and a fluorescence standard of quinine sulfate in 0.1M H$_2$SO$_4$ (Table 1 and FIG. 2). The single-stranded oligonucleotides have quantum yields of fluorescence emission ranging from $\Phi_{em}=0.01$-0.03, all brighter than the free 8-DEA-tC nucleoside by up to a factor of five. Addition of the complementary sequences and duplex formation results in further fluorescence increase in all sequences, up to $\Phi_{em}=0.12$ for sequence GC. This quantum yield is 20-fold greater than that of the free 8-DEA-tC nucleoside, the largest such increase reported to date for a fluorescent nucleoside analogue.

Correct base pairing is essential to the increased $\Phi_{em}$ in the duplex. Mispairing 8-DEA-tC with A resulted in only a modest, less than 2-fold increase in $\Phi_{em}$, and placing 8-DEA-tC opposite an abasic site gave a $\Phi_{em}$ effectively the same as for the free nucleoside. The three highest quantum yields observed for duplex oligonucleotides containing 8-DEA-tC all have guanine as the 5'-neighboring base.

Figure 3:
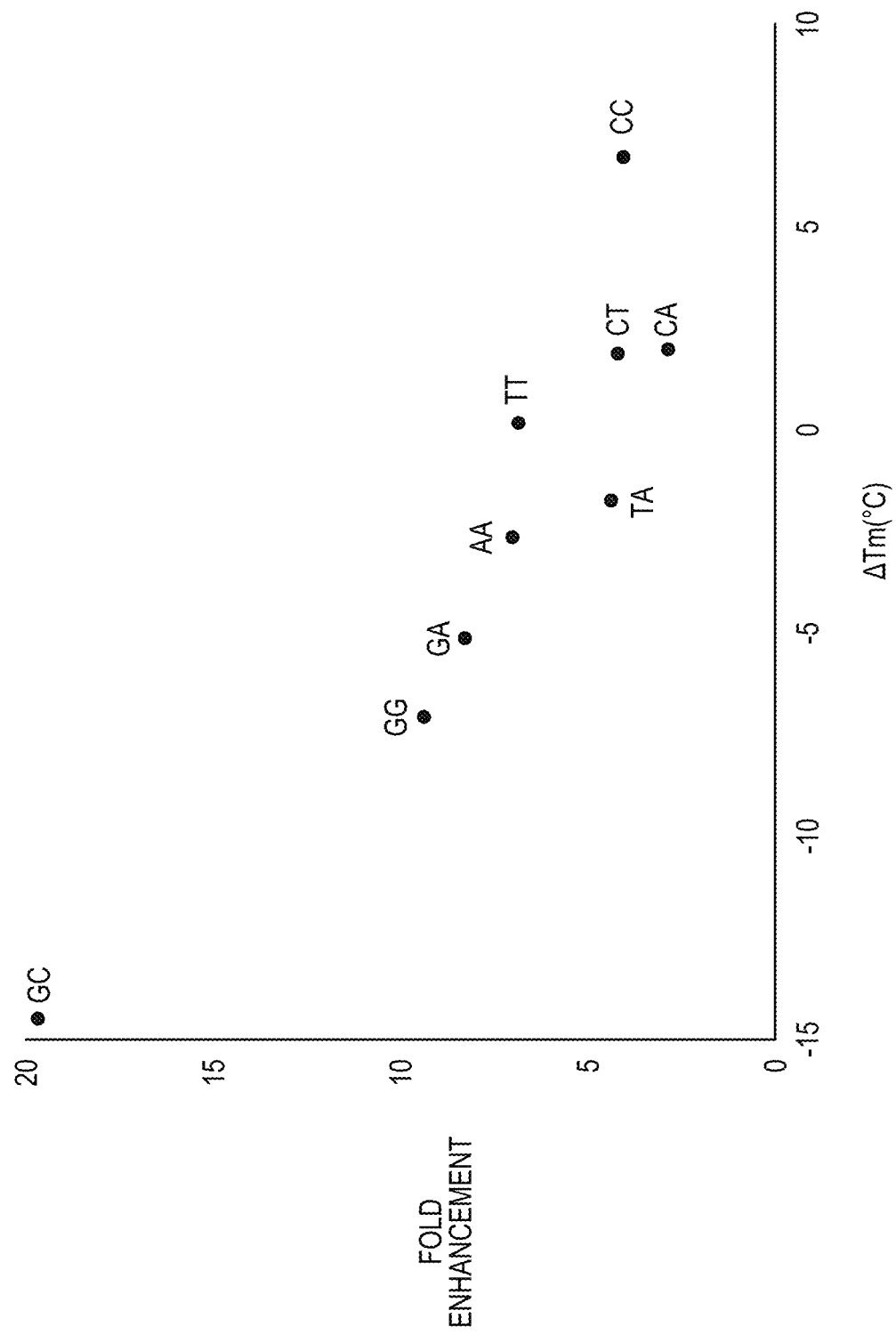
FIG. 3. Correlation between the fold enhancement of $\Phi_{em}$ from 8-DEA-tC nucleoside to double-stranded DNA and the $\Delta T_m$ (Table 1) for each sequence.

The brightest sequence, GC, is noteworthy for three reasons. First, it is known that intercalated ethidium has a greater $\Phi_{em}$ in poly(dG-dC) than in natural DNA sequences, paralleling our observations for 8-DEA-tC. Second, the $\lambda_{max,abs}$ is significantly blue-shifted as compared with any other sequence. Third, the $\Delta T_m$ measurements show a striking inverse correlation to the percent quantum yield increase from free nucleoside to duplex (FIG. 3). Electronic interactions between 8-DEA-tC and neighboring bases are therefore strongly tied to the fluorescence turn-on effect.

Figure 4:
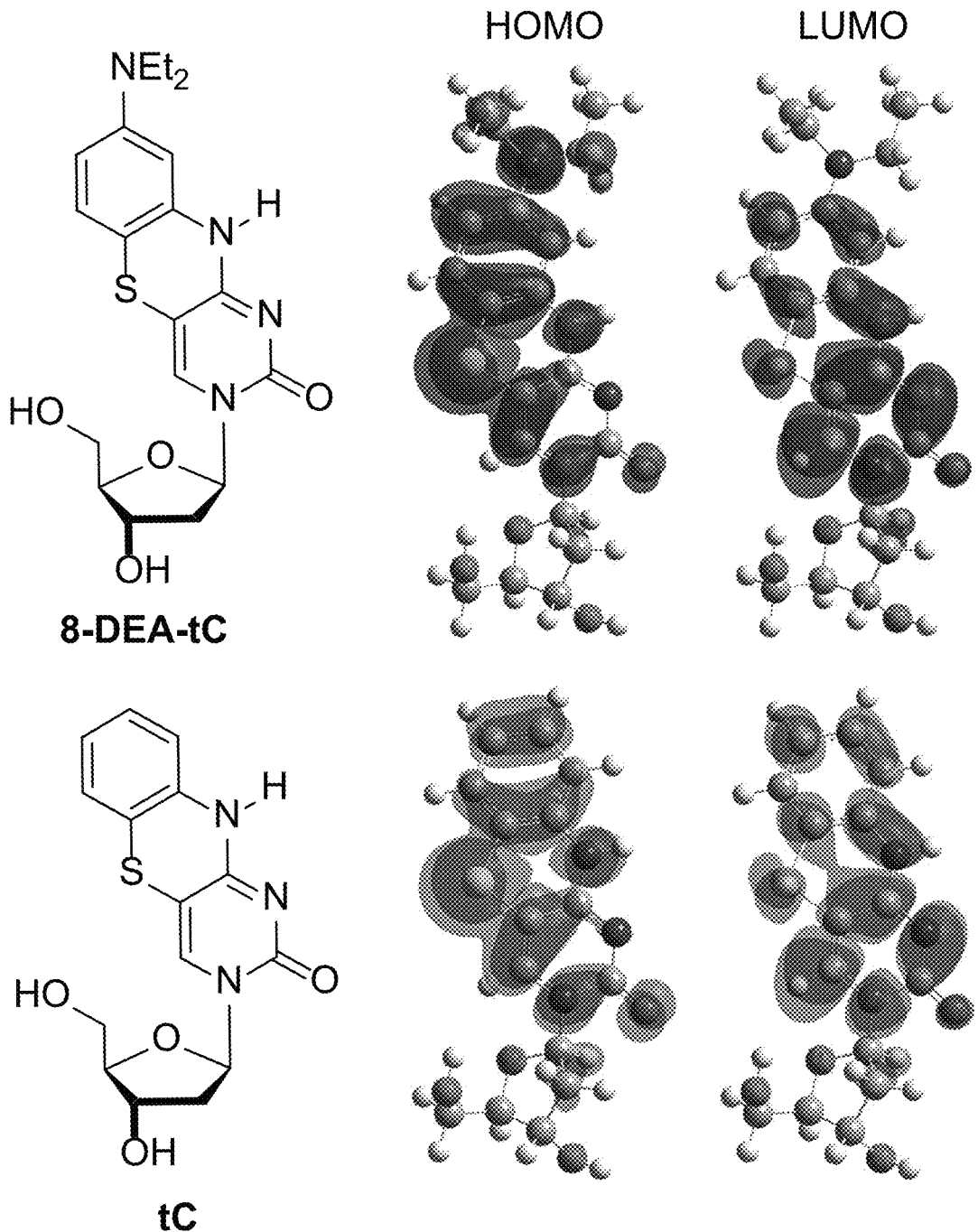
FIG. 4. Molecular orbital calculations comparing HOMO and LUMO orbitals of the tC and 8-DEA-tC nucleosides.

Subsequently it was determined which aspects of the 8-DEA-tC nucleobase structure explain the photophysical properties. First, it was noted that SYBR Green I, ethidium bromide, and Luedtke's $^{DMA}$T nucleoside all have pronounced push-pull electronic motifs that can stabilize a charge separated Si state, and such a motif is not present in the parent tC. To test whether the diethylamino group in 8-DEA-tC enhances such character, the appearance and energies of the HOMO and LUMO orbitals calculated by DFT ($B_3$LYP/cc-pVDZ) at the optimized geometries was examined (FIG. 4; computational details are in the Examples section below). These calculations show that the HOMO and LUMO of parent tC are distributed across the arene. In contrast, the HOMO of 8-DEA-tC is much more polarized towards the diethylaminobenzene ring and the LUMO towards the pyrimidine ring, indicating a push-pull character. The electronic modification imparted by the diethylamino group therefore makes this nucleoside's π system more electronically similar to SYBR Green I, ethidium bromide, and $^{DMA}$T.

TABLE 1

Properties of single- and double-stranded oligonucleotides containing 8-DEA-tC in 1x PBS buffer pH 7.4.[a]

| Sequence Name[b] | Sequence | ss Φem | ds Φem | ds $\lambda_{max,abs}$/ nm (ss) | ds $\lambda_{max,em}$/ nm (ss) | $T_m$/ ° C. | $\Delta T_m$/ ° C.[c] |
|---|---|---|---|---|---|---|---|
| GA | 5'-CGC-AGX-ATC-G-3' (SEQ ID NO: 10) | 0.020 | 0.050 | 422 (425) | 499 (499) | 50.7 | -5.1 |
| CT | 5'-CGC-ACX-TTC-G-3' (SEQ ID NO: 11) | 0.020 | 0.025 | 414 (413) | 492 (495) | 54.7 | +2.0 |
| GC | 5'-CGC-AGX-CTC-G-3' (SEQ ID NO: 12) | 0.032 | 0.12 | 348 (425) | 500 (499) | 49.1 | -14.5 |
| CA | 5'-CGC-ACX-ATC-G-3' (SEQ ID NO: 13) | 0.014 | 0.017 | 410 (420) | 494 (493) | 57.4 | +2.1 |
| GG | 5'-CGC-AGX-GTC-G-3' (SEQ ID NO: 14) | 0.027 | 0.056 | 400 (415) | 499 (498) | 58.2 | -7.0 |
| CC | 5'-CGC-ACX-CTC-G-3' (SEQ ID NO: 15) | 0.013 | 0.024 | 413 (421) | 496 (496) | 60.2 | +6.7 |
| TA | 5'-CGC-ATX-ATC-G-3' (SEQ ID NO: 16) | 0.014 | 0.026 | 420 (417) | 495 (495) | 48.7 | -1.6 |
| TT | 5'-CGC-ATX-TTC-G-3' (SEQ ID NO: 17) | 0.025 | 0.041 | 416 (413) | 495 (495) | 48.5 | +0.2 |
| AA | 5'-CGC-AAX-ATC-G-3' (SEQ ID NO: 18) | 0.008 | 0.042 | 410 (415) | 498 (497) | 48.4 | -2.6 |
| AA mismatch[d] | 5'-CGC-AAX-ATC-G-3' (SEQ ID NO: 18) | 0.008 | 0.015 | 417 (415) | 501 (497) | 33.1 | +9.6 |
| AA AP site[e] | 5'-CGC-AAX-ATC-G-3' (SEQ ID NO: 18) | 0.008 | 0.007 | 421 (415) | 466 (497) | 36.9 | n.d[f] |
| tC parent AA[g] | 5'-CGC-AAtC-ATC-G-3' (SEQ ID NO: 19) | 0.11 | 0.11 | 389 (390) | 501 (502) | 55.3 | +4.3 |

[a]Detailed procedures for photophysical measurements are given in the Examples section below, ds = double-stranded; ss = single-stranded.
[b]Sequences named for neighboring bases.
[c]$T_m$ for natural DNA duplex subtracted from $T_m$ for the 8-DEA-tC-containing duplex.
[d]AA sequenced annealed to 5'-CGA-TAT-TGC-G-3' (SEQ ID NO: 20) (8-DEA-tC opposite A).
[e]AA sequenced annealed to 5'-CGA-T(dSpacer)T-TGC-G-3' (SEQ ID NO: 21) (8-DEA-tC opposite the dSpacer surrogate for an abasic site, AP).
[f]Temperature-dependent CD changes were nonsigmoidal for the natural DNA strand and $T_m$ could not be determined.
[g]Sequence AA made with parent tC in place of 8-DEA-tC.

Examination of four potential quenching mechanisms for 8-DEA-tC that might be attenuated in the duplex that could explain the fluorescence enhancement was subsequently performed. These mechanisms are solvent quenching, chloride quenching, a molecular rotor effect, and excited-state proton transfer. As described above, 8-DEA-tC is approximately twice as sensitive to quenching by protic solvent as the parent tC, which is not sufficient to explain a 20-fold fluorescence increase. Our CD data show that the B form of DNA is intact when 8-DEA-tC is present opposite an abasic site, but there is no fluorescence increase as compared with the free nucleoside. Desolvation of the 8-DEA-tC nucleoside when base stacked therefore does not explain the fluorescence turn-on.

To test the ability of the duplex to attenuate chloride quenching of 8-DEA-tC, a Stern-Volmer analysis was performed using the 8-DEA-tC nucleoside and the TT duplex oligonucleotide (see Examples section below). To our surprise, the 8-DEA-tC nucleoside is more fluorescent with increasing chloride concentration, likely owing to salt-induced changes in solvation. In contrast, chloride has a modest quenching effect on 8-DEA-tC when present in the matched TT duplex. These results rule out the possibility that protection against chloride quenching contributes to the fluorescence turn-on effect.

It was hypothesized that the C—N bond appending the diethylamino group to tC may provide a molecular rotor effect, enabling non-emissive relaxation coupled to conformational change at the excited state. While molecular modeling suggests that the diethylamino group would be relatively free to rotate in a duplex oligonucleotide (see Examples section below), water dynamics in the DNA major groove are known to slowed by up to 50-fold as compared with bulk water. For this reason, it was hypothesized that slowed water dynamics in the major groove of the duplex could cause an increase in the fluorescence of 8-DEA-tC. To test this hypothesis, a comparison of the solvent viscosity sensitivity of fluorescence of the 8-DEA-tC nucleoside with parent tC and 9-(2,2-dicyanovinyl)julolidine (DCVJ, a frequently used reference compound for viscosity effects on fluorescence) using mixtures of glycerol and methanol was performed (see Examples section below). It was found that 8-DEA-tC, unlike parent tC, has fluorescence intensity that is positively correlated to viscosity, but the response of DCVJ is three-fold greater.

Other nucleoside analogue molecular rotors investigated by Tor are more sensitive to viscosity than 8-DEA-tC, but they lose $\Phi_{em}$ when base stacked. Moreover, when 8-DEA-tC is present opposite an abasic site in a duplex that maintains B form, there is no fluorescence increase. 8-DEA-tC is a molecular rotor type fluorophore, but the fluorescence increase that was observed in duplex DNA cannot be attributed to restricting the C—N bond rotation.

To test the influence of the duplex on excited-state proton transfer, $\Phi_{em}$ in deuterated 1X PBS buffer was measured, where a kinetic isotope effect slows proton transfer. In deuterated buffer, the 8-DEA-tC nucleoside is twice as bright: $\Phi_{em}$=0.012. But buffer deuteration causes almost no quantum yield increase in the TT duplex: $\Phi_{em}$=0.045. This result shows that the duplex protects 8-DEA-tC from excited state proton transfer, clearly a significant factor contributing to the fluorescence turn-on.

Figure 5:
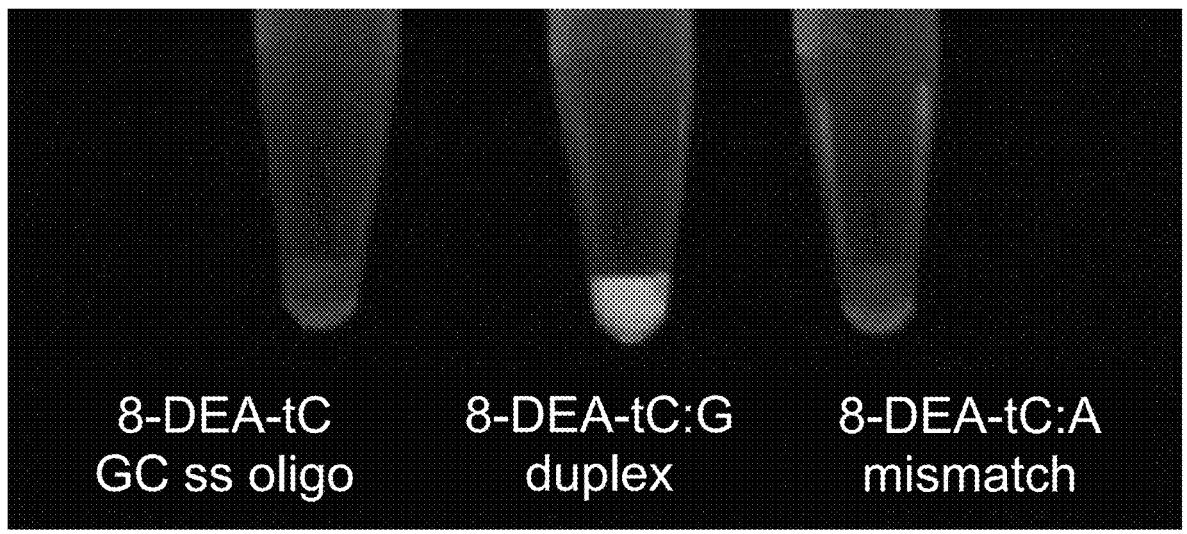
FIG. 5. Visual discrimination of single nucleotide polymorphism by 8-DEA-tC. Samples were prepared in 0.5X PBS buffer and illuminated by a hand-held UV lamp. Left to right: 8-DEA-tC ss GC oligo (Table 1), GC oligo annealed to its matched complement, GC oligo annealed with an 8-DEA-tC:A mismatch.
Figure 6:
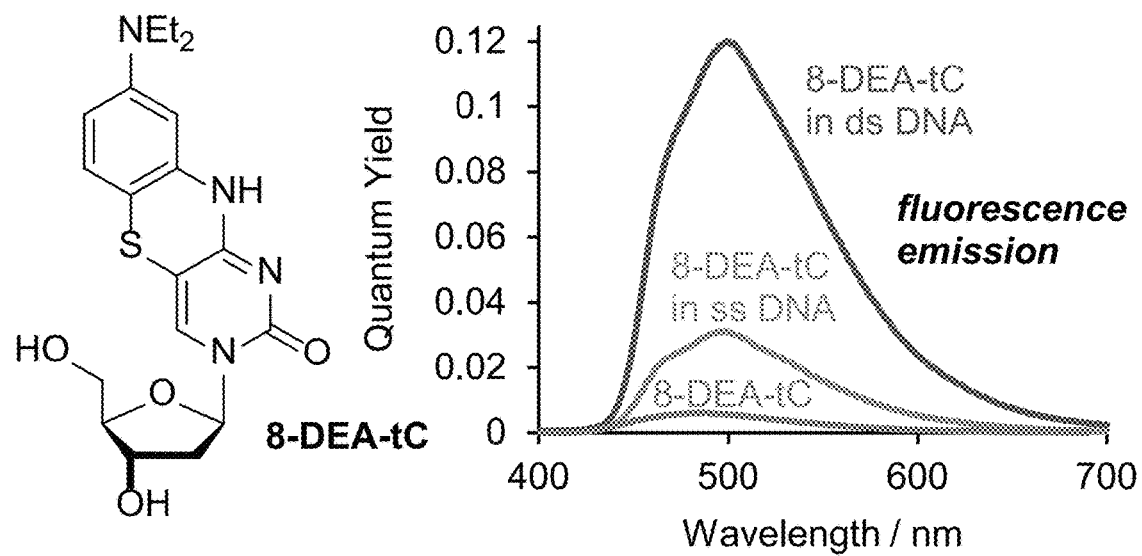
FIG. 6. 8-DEA-tC quantum yield when present as a free nucleoside, when included in single-stranded DNA, and when that single-stranded DNA with 8-DEA-tC included is annealed to a matched, complementary strand of DNA.
Figure 7A:
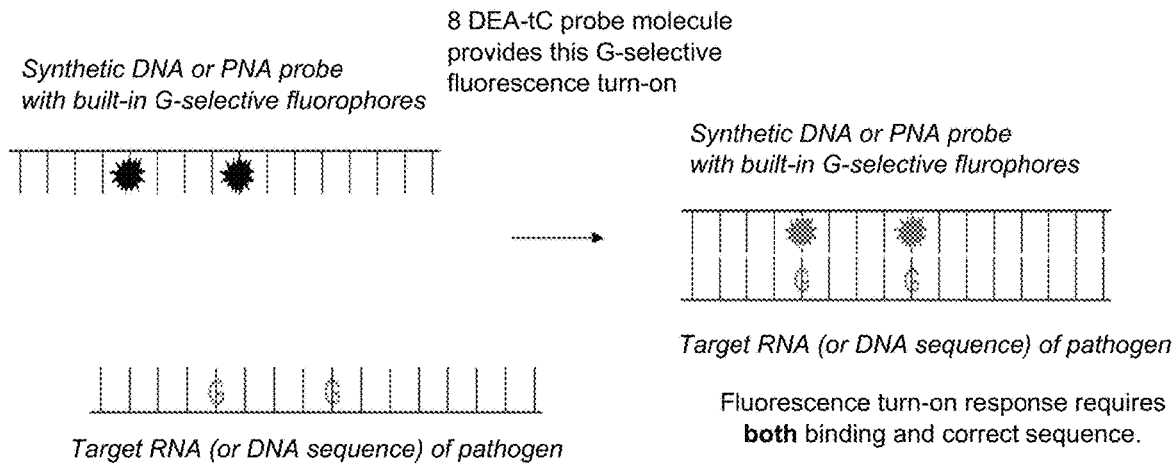
FIG. 7A-7B. (A) Existing fluorescence hybridization probes detect DNA and RNA targets by binding and carrying along a fluorophore reporter. This disclosure replaces a tethered reporter with a new type of fluorophore that is integrated direction in the DNA/RNA sequence and is able to become fluorescent only when the sequence matches. (B) Development of nucleoside analogues that can be delivered to living cells and become fluorescent when incorporated into nascent DNA or RNA.
Figure 7B:
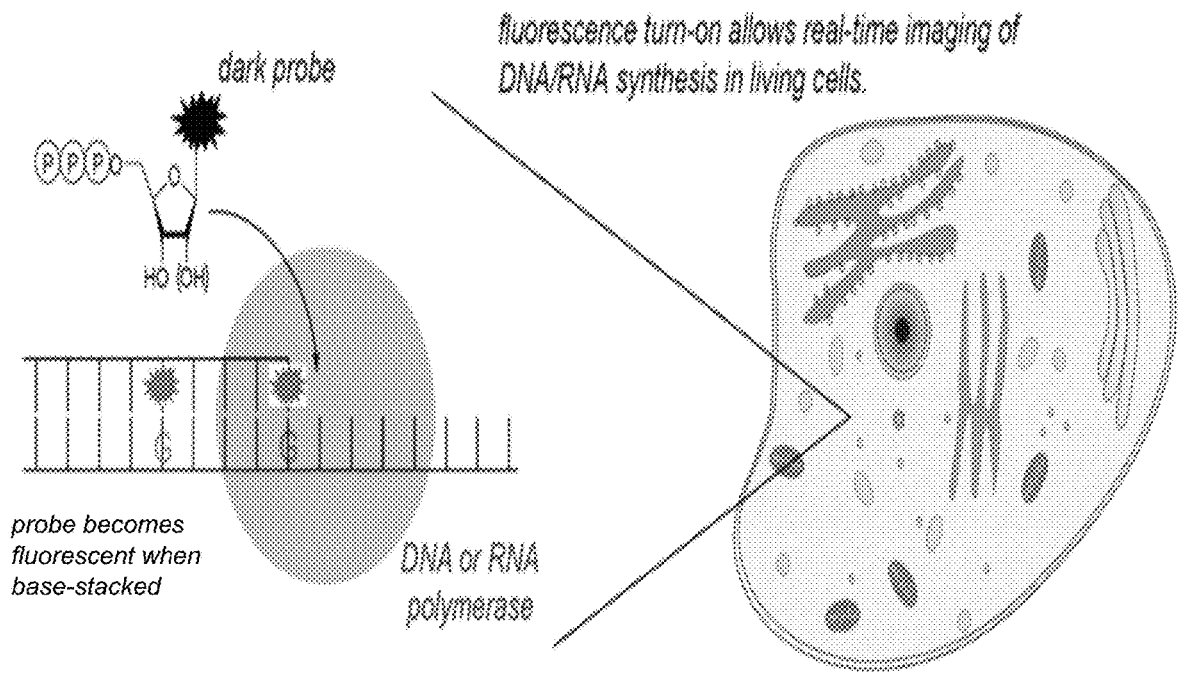

Next, the ability of 8-DEA-tC to distinguish single nucleotide by a visible fluorescence response was tested (FIG. 5). 0.26 mM solutions of GC oligo in 0.5X PBS buffer were prepared with the GC oligo alone, a duplex with the matching complement, and a duplex with an 8-DEA-tC mismatch. Visual inspection of the samples irradiated with a hand-held UV lamp clearly shows that the perfectly matched duplex is indicated by a large increase in fluorescence.

This disclosure provides that 8-DEA-tC is a fluorescent turn-on probe for base pairing and, when converted to the triphosphate, and also as a probe for enzymatic DNA synthesis.

The above examples focus on the DNA nucleotide, where Y=H (Formula B). This disclosure also describes the RNA version, where Y=OH. This RNA version may have important applications in antiviral drug development, amongst other things. These applications are not necessarily for a drug proper, but can be used in biochemical studies on drug metabolism and on- and off-target effects such as mitochondrial toxicity. They may also be useful for developing new types of drug screening assays.

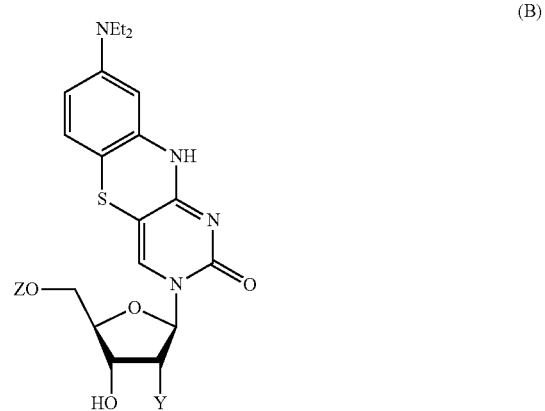

(B)

Figure 11:
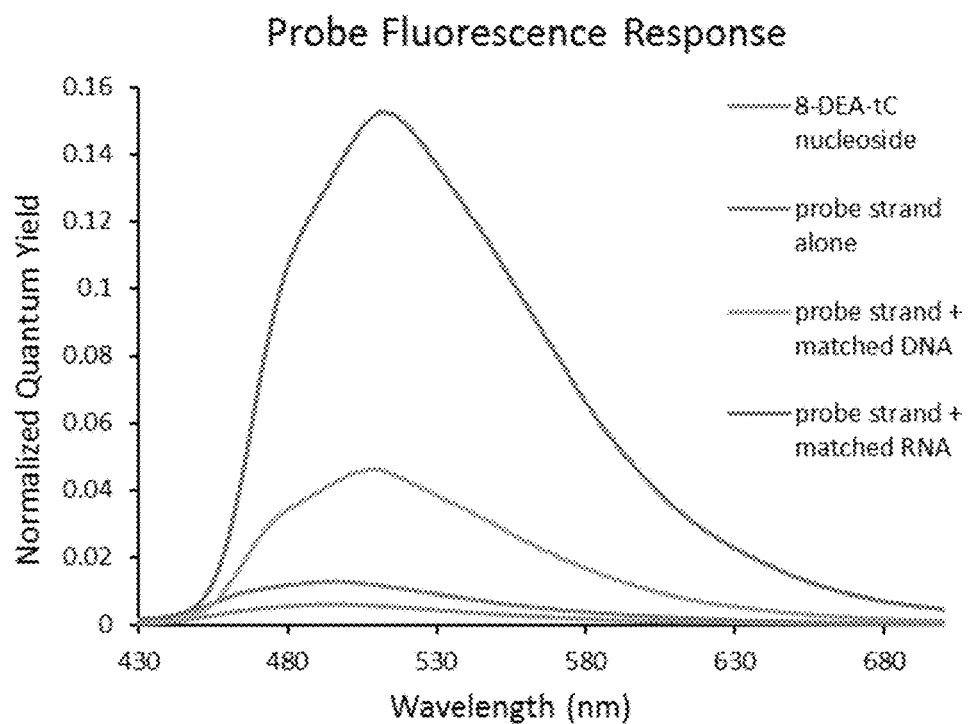
FIG. 11. Probe fluorescence response.

The RNA version (Y=OH) has been synthesized and characterized. Spectroscopic evidence exists that shows RNA applications can be successful. The shape (conformation) of double-stranded nucleic acids can vary, and there are three major forms: A, B, and Z. Double-stranded DNA is naturally B form. Double-stranded RNA is naturally A form. And a DNA-RNA heteroduplex also naturally takes A form. For that reason, it is possible to use a DNA-RNA heteroduplex to predict fluorescence properties in pure RNA. This procedure has been performed with existing DNA probes, where it was observed that the fluorescence turn-on effect works at least three times better that what was shown for double-stranded DNA results. This new result suggests that the probes can work even better for RNA applications than for DNA applications. A supporting image is shown in FIG. 11. The sequence for the probe strand used to generate this data is 5'-CGC-AA(8-DEA-tC)-ATC-G-3' (SEQ ID NO: 41) and fluorescence responses were measured in 1x PBS buffer at pH 7.4.

Fluorescence-Based Real-Time Visualization of DNA Synthesis in Living Cells

The synthesis and degradation of nucleic acids in living cells is a central part of metabolism that is critical to understanding the biology of healthy cells and diseases, including cancer and viral infection. This disclosure provides the first biophysical method for real-time monitoring of nucleic acid synthesis, metabolism and degradation in real time in living cells, with single cell resolution. The outcome can be broadly applicable to future studies of disease and efforts to develop new therapeutics.

Studies of DNA and RNA synthesis and degradation are useful for understanding how individual cells respond to exogenous stress or disease. Single-cell resolution is valuable because the responses may differ between cells in a tissue. Almost all currently available methods for tracking nucleic acid synthesis in cells use 5-bromo-(2'-deoxy)-uridine or ethynyl-modified nucleoside analogues. Both methods rely on a staining step, using a fluorescent antibody or a click reaction. This step is toxic and kills the cells, and thus can only be used for single time point measurements. The disclosed probes enable, among other things, the monitoring of cellular DNA and RNA synthesis and DNA synthesis by viral reverse transcriptases, and the assessment of toxicity and fluorescence signal strength using pulse-chase methods. The 8-DEA-tC probes can be delivered to living cells using phosphate group masking strategies borrowed from medicinal chemistry or using transfection methods. Polymerase and reticulocyte lysate assays can be used to measure the kinetics and fidelity of probe insertion during DNA/RNA synthesis.

Based on known nucleotide prodrug methods, nucleoside kinases, which add the α-phosphate group, generally have the least compatibility with unnatural nucleosides and are the bottleneck to the efficient generation of unnatural nucleoside triphosphates in cells. UMP-CMP kinase and nucleoside diphosphate kinases have much broader substrate scopes. For these reasons, the delivery of a masked nucleoside monophosphate can lead to competitive concentrations of d(8-DEA-tC)TP in cells. At least two chemical approaches provide the desired prodrugs: para-acyloxylbenzyl (PAOB) esters and ProTides. Both masking groups undergo ester hydrolysis catalyzed by cytoplasmic esterases, leading to unmasking once inside of cells (Scheme B).

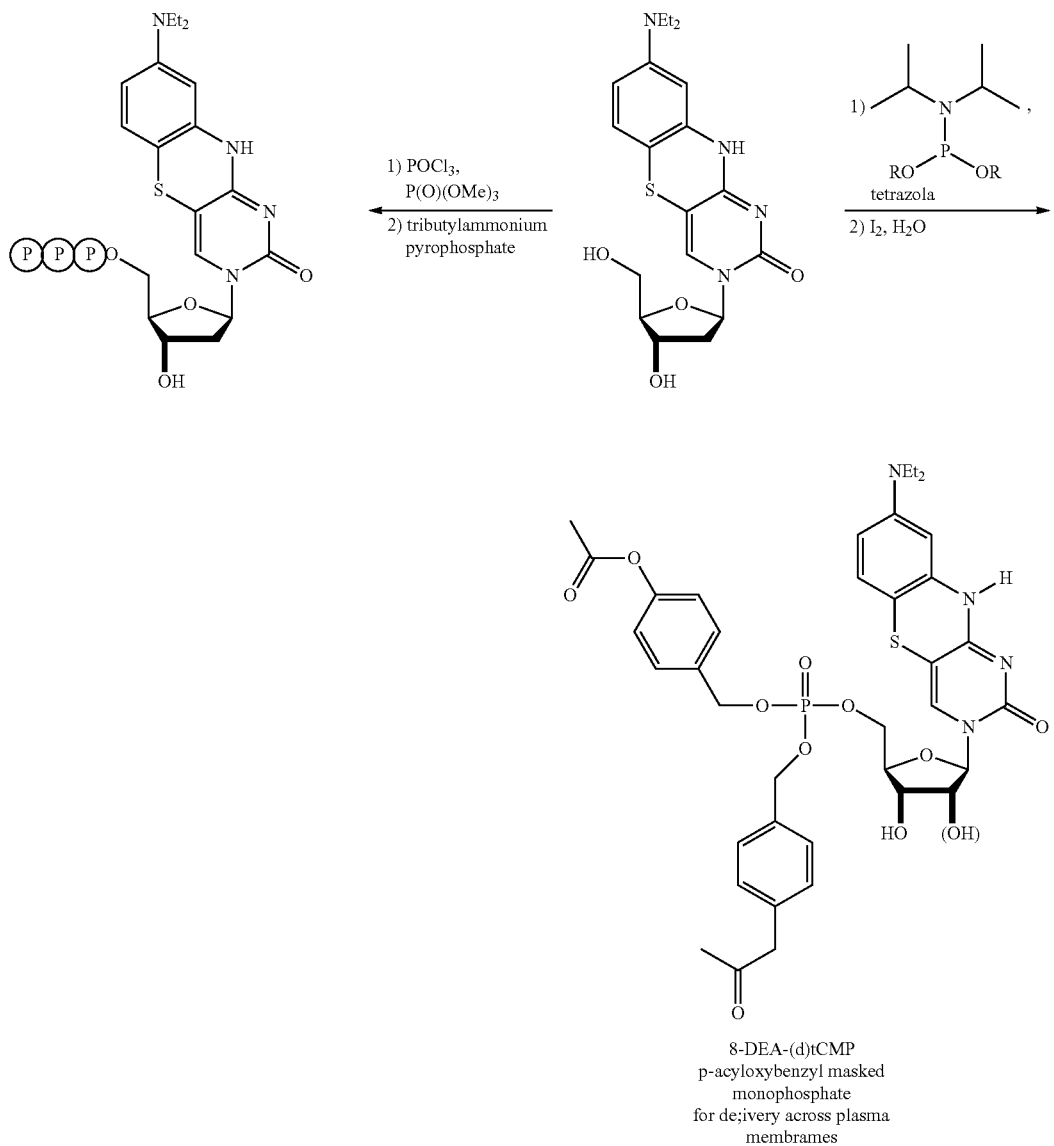

Scheme B. The 8-DEA-tC nucleoside can be advanced to prepare the triphosphate using standard chemistry or can be converted into a masked NMP for delivery.

8-DEA-(d)tCMP
p-acyloxybenzyl masked
monophosphate
for de;ivery across plasma
membrames Using the same TMS-protected tricyclic cytosine as for the 2'-deoxy, the ribonucleoside can be prepared using standard ribosylation conditions. This nucleotide can be converted readily to the triphosphate or the PAOB esters as described. The 8-DEA-tCMP ProTide can also be prepared as an alternative since it can also diffuse through the plasma membrane and be converted into the monophosphate in the cytoplasm (Scheme C).

markers for identifying pathogens and genetic diseases. Modern sequencing methods are powerful and sensitive, but slow and complex. There is a great need for improvement on detection reagents that can rapidly and accurately identify specific sequences of DNA or RNA in a robust and field-deployable capacity. Existing methods for rapid DNA/RNA sequence detection often have problems with distinguishing closely related sequences, a significant limitation.

Scheme C. Ribosylation of the 8-DEA-tC nucleobase and synthetic elaboration provides the ribosyl triphosphate or a masked monophosphate for delivery.

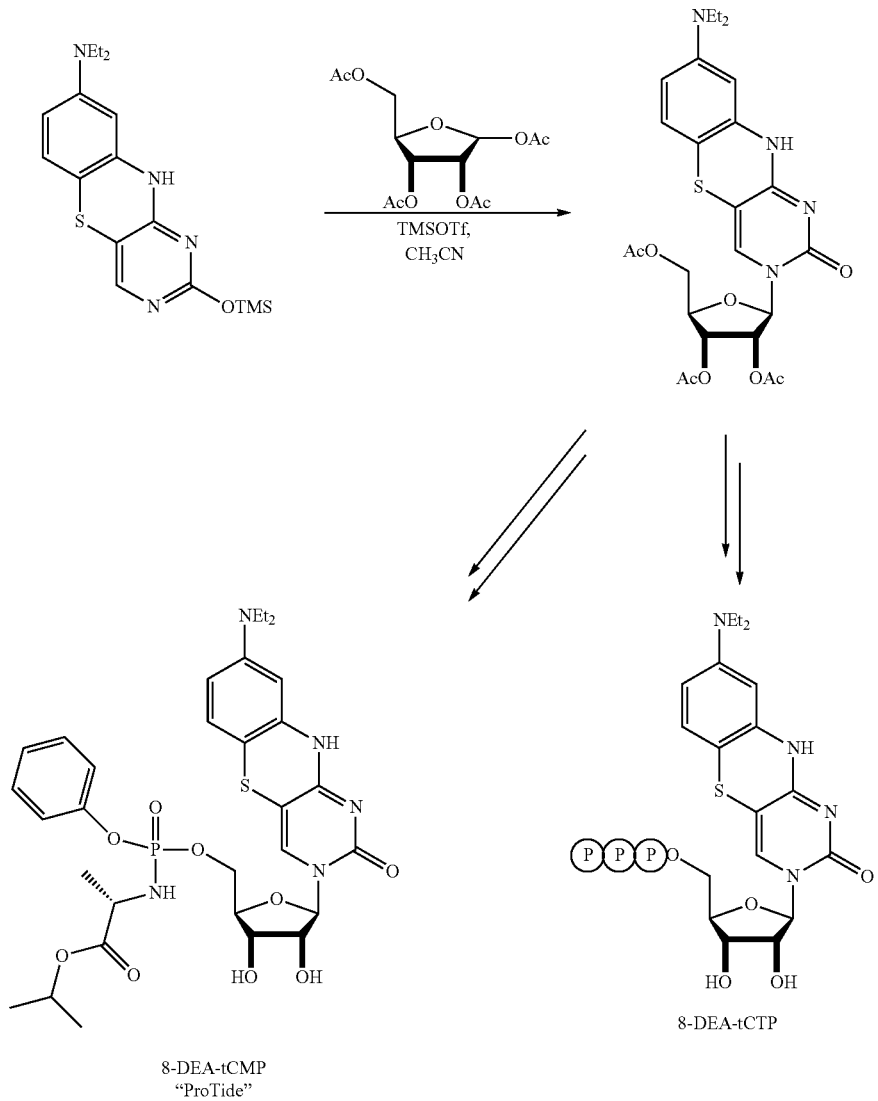

Another alternative to deliver the probe into cells uses electroporation or one of many other transfection methods, which render cells temporarily leaky and have been shown to allow nucleotide uptake. A third alternative applies a modified PAOB synthesis for delivering 8-DEA-tC as a masked triphosphate.

PNA-Based Fluorescence Turn-on Hybridization Probes

Figure 12:
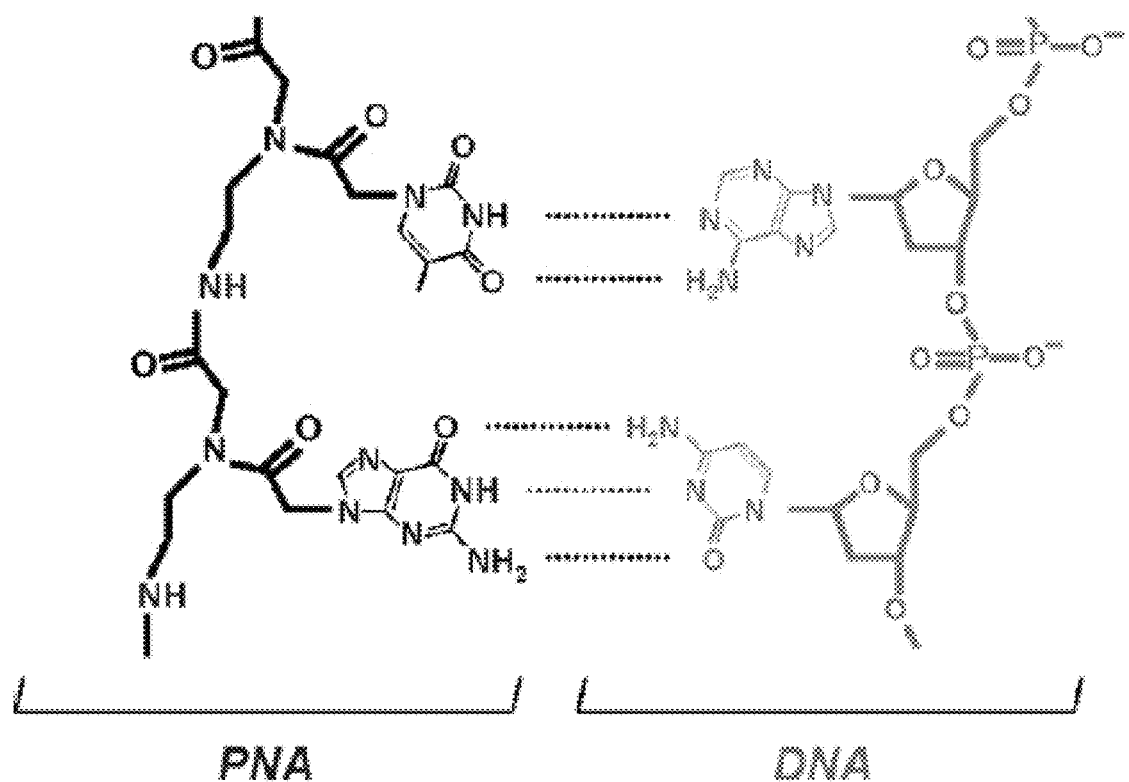
FIG. 12. Peptide nucleic acids (PNA) binding complementary sequences of DNA/RNA. Affinity of complementary PNAs to DNA or RNA is higher than natural complementary sequences of DNA/RNA.
Figure 13:
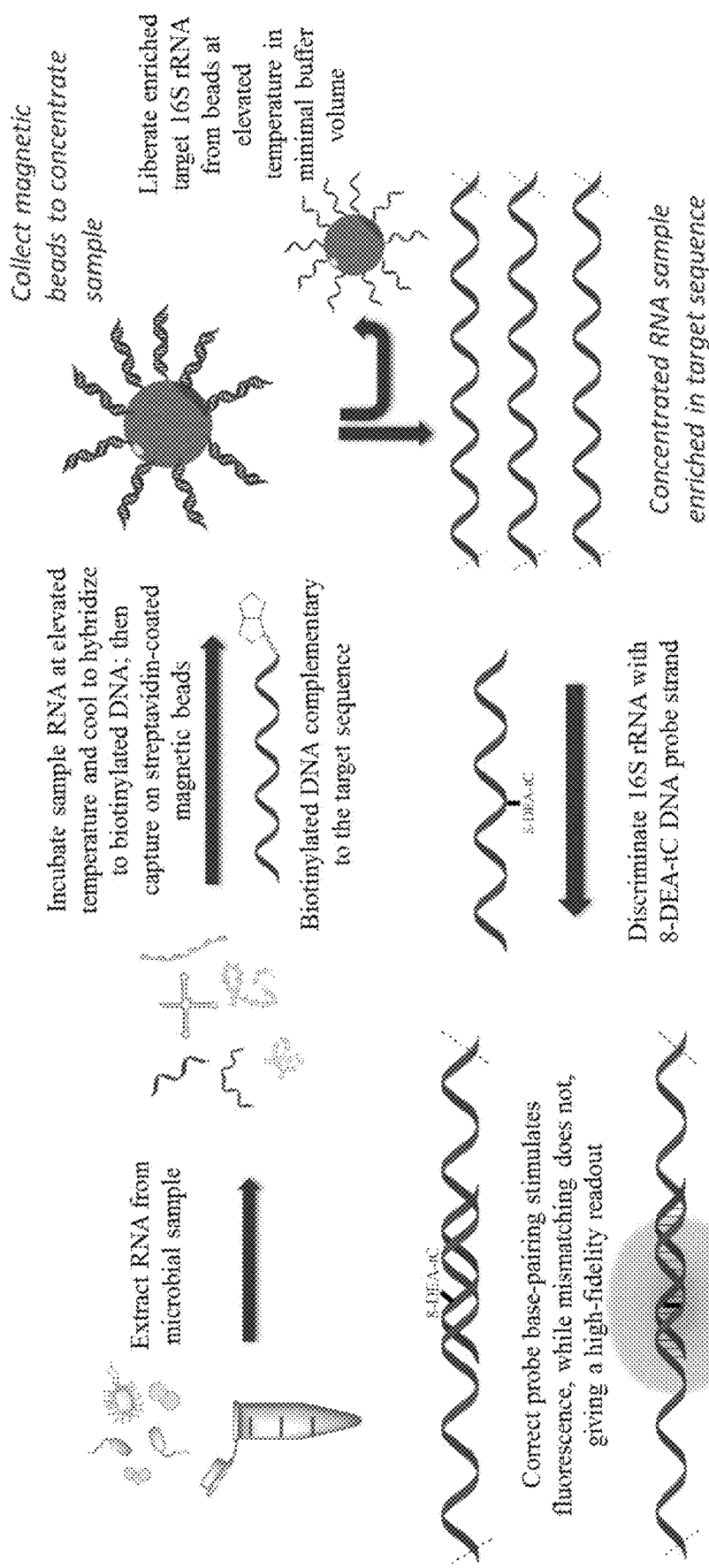
FIG. 13. Sample enrichment using magnetic beads followed by fluorescence detection with 8-DEA-tC hybridization probe.

This disclosure provides a new way to use fluorescence to detect and discriminate DNA and RNA sequences quickly, robustly, and with high fidelity. Because they store the genetic code, DNA and RNA are the most broadly useful Included with this disclosure is an application for peptide nucleic acids (PNA) (FIG. 12). A PNA variant of the 8-DEA-tC fluorescence turn-on probes can be prepared to take advantage of PNA's greater affinity for DNA and RNA targets, and therefore used to improve upon signal amplification and sample enrichment procedures (FIG. 13). This affinity translates to enhanced sensitivity and specificity for matched sequences. Peptide nucleic acids have been prepared in the past using other fluorescent cytidine analogues (however, these analogues do not have a fluorescence turn-on capability), and have be shown to have enhanced affinity and specificity for DNA and RNA sequences.

The 8-DEA-tC fluorescence turn-on probe can be used for making PNA and γPNA versions of the disclosed fluorescent probe. The monomers shown below can be readily synthesized, which could then be incorporated into (γ)PNA using well-established methods (*J. Org. Chem.*, 2011, 76, 5614).

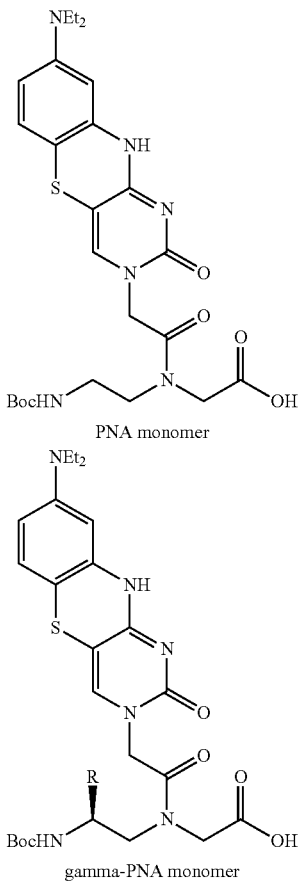

Synthesis of PNA monomers can be accomplished using simple adaptations of known chemistry from the disclosed fluorescent 8-DEA-tC cytosine analogue (Scheme 2). The analogue can be converted to the acetic acid derivative (middle compound of Scheme 2) using methods closely following those reported for related cytidine analogues (*J. Phys. Chem.* B, 2003, 107, 9094). Last, this derivative can be coupled to peptidic PNA precursors as shown, closely following established methods (*J. Org. Chem.*, 2001, 2, 1781). The R groups shown in Scheme 2 can be R=H or a variety of other groups (e.g. an oligoethylene glycol) to give PNA or γPNA, respectively. Derivatives of the disclosed cytosine compounds could easily be incorporated into PNA using the same or similar chemistry. Most notably, changing the ethyl groups (Et) to other alkyl groups (methyl, propyl, isopropyl, etc.) could give compounds with equivalent or similar fluorescence turn-on properties.

Therefore, PNA probes can be prepared from 8-DEA-tC and certain sequences of the DNA, for example, GC, GA, AA, TA, CA, and CC (Table 1). This set of oligonucleotides show that there is some sequence dependence to these fluorescence turn-on effects insofar as that the neighboring nucleobases 5' and 3' to 8-DEA-tC influence the photophysics, with the 5' neighbor having the stronger effect. The brightest duplex sequences have G as the 5' neighbor. GC is the brightest overall sequence, but the AA sequence has a slightly greater fluorescence turn-on response to annealing (FIG. 13). Because oligonucleotide probe strands typically need to be about 20 nucleotides in length to be specific (a statistical result of genome sizes), there are multiple design options for oligonucleotide probes that can include 8-DEA-tC.

These PNA probes can be used, for example, for sample enrichment. In one strategy, streptavidin-conjugated magnetic beads are used to capture and enrich the target DNA or RNA. After target elution from the beads in a much smaller volume, an 8-DEA-tC oligonucleotide fluorescence probe can be used to quantify the target with high specificity and sensitivity (Example 8).

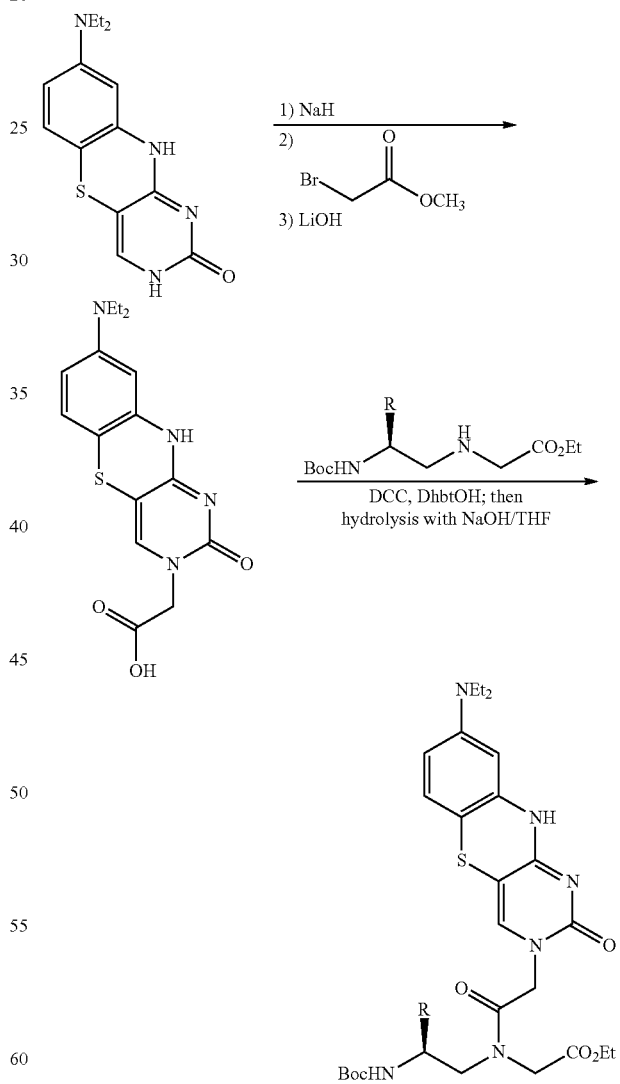

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Synthesis and Characterization of Compounds

All reagents and chemicals used were purchased from Acros Organics and Fisher Chemical at ACS grade or higher quality and used as received without further purification, except as noted. 5-Amino-2-methylbenzothiazole was obtained from Alfa Aesar, 2-Cyanoethyl-N,N,N',N'-tetraisopropylphosphorodiamidite was obtained from Sigma-Aldrich. Solvents used for UV/vis and fluorescence measurements were spectrophotometric grade or were aqueous buffers prepared using Milli-Q water.

NMR ($^{1}$H and $^{13}$C) spectra were acquired on Varian 400 MHz and a Varian 500 MHz NMR spectrometers and recorded at 298 K. Chemical shifts are referenced to the residual protio solvent peaks and given in parts per million (ppm). Splitting patterns are denoted as s (singlet), d (doublet), dd (doublet of doublet), t (triplet), q (quartet), and m (multiplet). Fluorescence measurements were recorded on a PTI Quantamaster QM-400 fluorescence spectrophotometer and corrected using the manufacturer's calibration files. Absorbance measurements were taken on a Shimadzu Pharma Spec 1700 UV-Vis spectrophotometer. CD spectroscopy was performed on an Aviv Model 420 and recorded at 298 K. High-resolution electrospray ionization (ESI) mass spectrometry was performed at the University of California, Riverside High Resolution Mass Spectrometry Facility using an Agilent LC-TOF in ESI mode.

Synthetic steps that required an inert atmosphere were carried out under dried nitrogen gas using standard Schleck techniques.

Synthesis of (8-DEA)tC

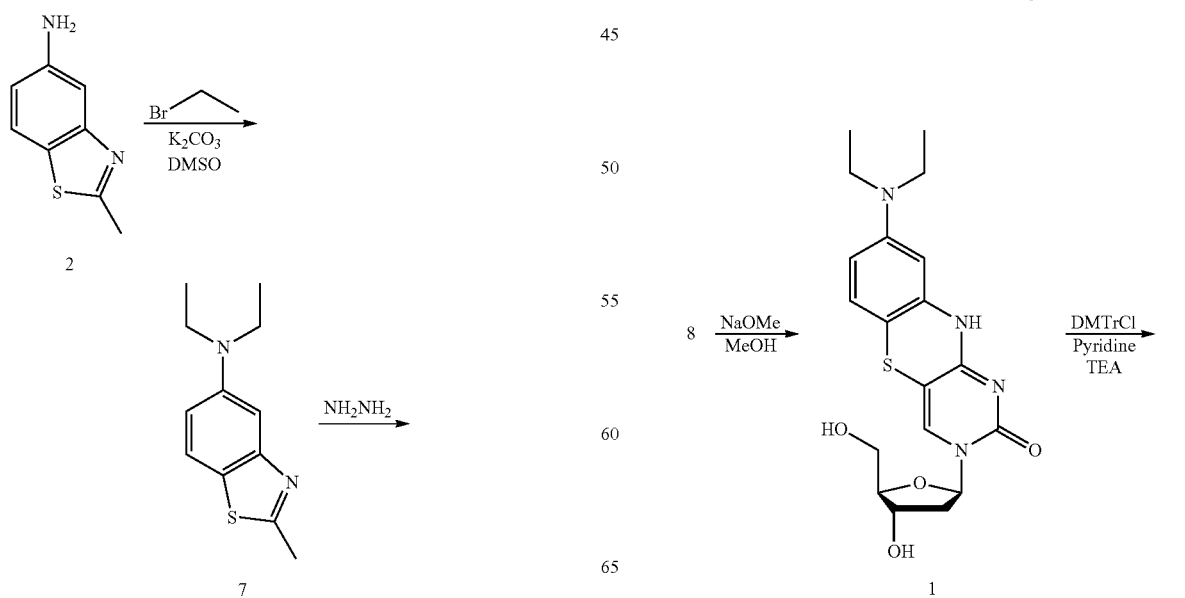

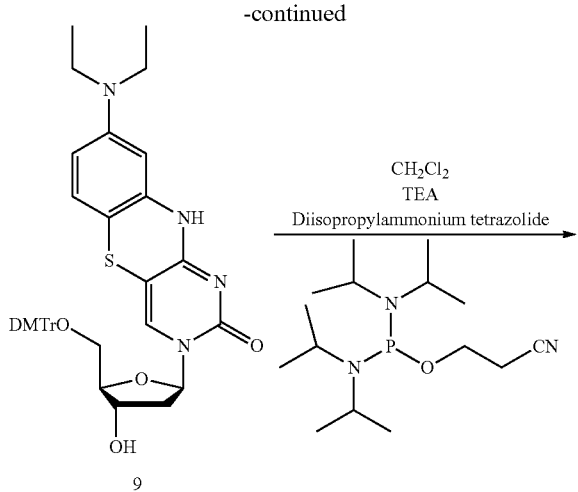

9

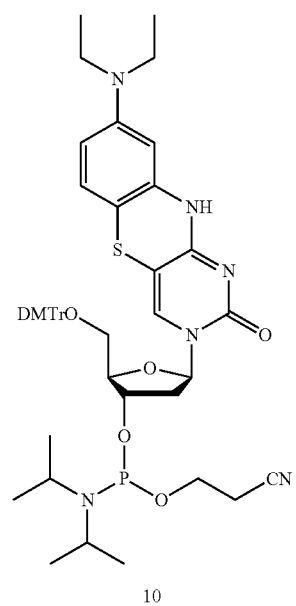

10

5-Diethylamino-2-methylbenzothiazole, 7

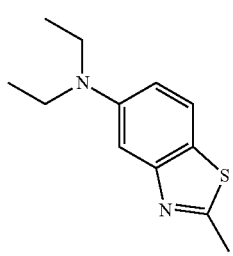

5-Amino-2-methylbenzothiazole 2 (5.58 g; 29.0 mmol) was placed in a dry 3 necked 100 mL round bottomed flask under nitrogen. To this was added a minimal amount of DMSO to achieve dissolution and the resulting mixture was stirred for 5 minutes. Anhydrous potassium carbonate was added to the reaction (3.26; 58 mmol) and bromoethane (4.33 mL, 58 mmol) and the reaction was heated to 80° C. and monitored by TLC (10% MeOH in dichloromethane). The reaction was found to be complete at 3 days. The reaction mixture was then diluted with and water extracted with ethyl acetate. The organics were combined and dried over sodium sulfate before solvent removal. Flash chromatography was performed using a gradient from hexane to ethyl acetate (0-100%) to yield the pure product as a yellow oil (5.1 g, 80%). $^1$H NMR (400 MHz, CDCl$_3$): δ 7.44 (d, J=8.9 Hz, 1H), 7.16 (d, J=2.5 Hz, 1H), 6.66 (d, J=8.9 Hz, 1H), 3.25 (m, J=7.1 Hz, 4H), 1.50 (t, J=7.0 Hz, 6H)$^{13}$C NMR (100 MHz, CDCl$_3$): δ 173.2, 148.7, 148.4, 121.8, 115.2, 113.8, 101.2, 44.9, 19.0, 12.2. (ESI) calcd. for C$_{12}$H$_{17}$N$_2$S [M+H]+ 221.1112, found 221.1106.

2-[(2-Amino-4-diethylaminophenyl)disulfanyl]-4-methoxyaniline, 3

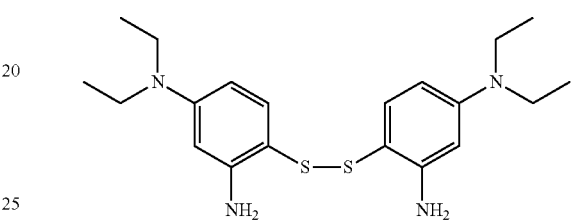

5-Diethylamino-2-methylbenzothiazole 7 (4.1 g, 18.6 mmol) was placed in a dry 100 mL round-bottomed flask under nitrogen. To this was added 25 mL of hydrazine hydrate and the reaction mixture was stirred at room temperature for ten minutes. The reaction mixture was then heated at 100° C. for 18 hrs. The reaction was monitored by TLC (10% MeOH in DCM) and found to be complete at 18 hours. The reaction was cooled to room temperature and rotovapped to dryness, then the product was extracted with EtOAC (3X). The organics were combined and dried over anhydrous sodium sulfate before evaporating to dryness. The product was purified by flash chromatography (1% MeOH in DCM). The pure product was found to be a yellow solid. (2.89 g, 79.5%)$^1$H NMR (500 MHz,CDCl$_3$): δ 7.08 (d, J=8.4 Hz, 2H), 6.00 (m, 4H), 4.25 (s, 4H), 3.32 (q, J=7.1 Hz, 8H), 1.15 (t, J=7.1 Hz, 12H)$^{13}$C NMR (100 MHz, CDCl$_3$): δ 150.7, 149.9, 138.6, 106.0, 103.1, 96.9, 44.3, 12.7. Due to this compound's propensity for oxidative degradation, no mass spectrum was obtained for this intermediate.

5-[(2-Amino-4-diethylaminophenyl)sulfanyl]pyrimidine-2,4(1H,3H)-dione, 4

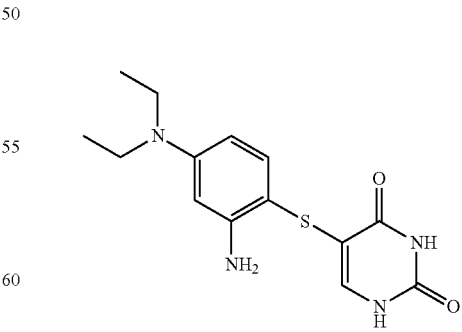

2-[(2-Amino-5-diethylaminol)disulfanyl]-5-diethylaminoaniline 3 (1.4 g, 3.6 mmol) was placed in a dry 3 neck 100 mL round-bottomed flask under nitrogen, to this was added triethylphosphine (1.79 mL of a 1M solution in THF) and water (32.0 uL). The reaction was stirred for 5 minutes at room temperature (25° C.). 5-Bromouracil (1.37 g, 7.2 mmol) and sodium carbonate (0.603 g, 7.2 mmol) were added to the reaction mixture and stirred at 120° C. The reaction was monitored by TLC (10% MeOH in DCM) and found to be complete at 18 hours. Upon completion the reaction mixture was cooled to room temperature and the resulting precipitate was filtered and rinsed with several portions of water and a few portions of ether. The material was purified by flash chromatography (0-10% MeOH in DCM). The solvent was removed by rotary evaporation. The product was found to be an off-white solid (800 mg, 36%) $^1$H NMR (400 MHz, $(CD_3)_2SO$): δ 11.27 (s, 1H), 10.91 (s, 1H), 7.14 (s, 1H), 7.11 (d, J=8.6 Hz, 1H), 6.02 (d, J=2.7 Hz, 1H), 5.93 (dd, J=8.7, 2.7 Hz, 1H), 5.25 (d, J=8.4 Hz, 1H), 3.31 (m, 1H), 3.24 (m, 4H), 1.06 (t, J=6.9 Hz, 6H). (ESI) cald. for $C_{14}H_{18}N_4O_2S$ [M+H]+ 307.1150, found 307.1237.

1H), 7.32 (s, 1H), 6.77 (d, J=8.6 Hz, 1H), 6.41 (d, J=2.4 Hz, 1H), 6.27 (dd, J=8.7, 2.4 Hz, 1H), 3.23 (m, 4H), 1.51 (t, J=6.9 Hz, 6H) $^{13}$C NMR (100 MHz, $(CD_3)_2SO$): δ 161.5, 155.9, 147.3, 137.8, 137.1, 126.9, 107.8, 100.7, 99.7, 94.8, 44.1, 12.6. (ESI) cald. for $C_{14}H_{16}N_4OS$ [M+H]+ 289.1045, found 289.1162.

8-Diethylamino-tC 3',5'-di-O-(p-toluoyl)-2'-deoxy-β-D-ribonucleoside, 8

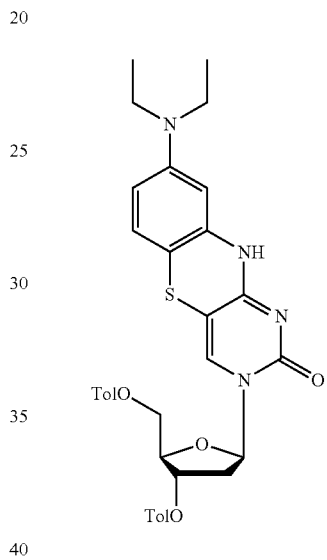

8-Diethylamino-3H-pyrimido[5,4-b][1,4]benzothiazin-2(10H)-one, 5

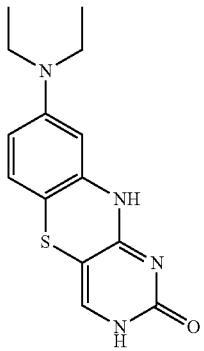 [SMILES: CCN(CC)c1ccc2c(c1)Nc1nc(=O)[nH]cc1S2]

5-[(2-Amino-4-diethylaminophenyl)sulfanyl]pyrimidine-2,4(1H,3H)-dione 4 (800 mg, 2.61 mmol) was placed in a clean dry 50 mL round-bottomed flask under $N_2$. To this was added 15 mL of 1-butanol and the reaction was heated to 120° C. for 10 minutes and then cooled to room temperature. Once cooled, concentrated HCl (1.5 mL) was added to the reaction and the reaction mixture was heated to 120° C.. The reaction was monitored by TLC (10% MeOH in DCM) and found to be complete at 24 hrs. Upon completion the reaction was cooled to room temp and quenched with 5% ammonium hydroxide. The reaction mixture was evaporated to dryness and the crude product was purified by flash chromatography to yield a yellow solid (0.733 g, 97%) $^1$HNMR (400 MHz, $(CD_3)_2SO$): δ 10.87 (s, 1H), 9.87 (s, 8-Diethylamino-3H-pyrimido[5,4-b][1,4]benzothiazin-2 (10H)-one 5 (346.1 mg, 1.2 mmol) was suspended in dry acetonitrile in a Schlenk tube under nitrogen. Bis(trimethylsilyl)acetamide (1.38 mmol) was added and the reaction mixture allowed to stir at 50° C. for 1 h until the starting material had completely dissolved and reacted to form the TMS ether, as indicated by a color change to orange. The reaction mixture was allowed to cool to room temperature and 3',5'-di-O-(p-toluoyl)-2'-deoxy-α-D-ribofuranosyl chloride, 6 (1.32 mmol) was added with stirring. The reaction mixture was cooled to 0° C. and tin(IV) chloride (0.24 mmol) was added dropwise. The reaction mixture was stirred at 0° C., then allowed to warm to room temperature, and the progress was tracked by TLC (10% $CH_3OH$ in $CH_2C_{12}$). The reaction was complete in 45 min. At this time, the mixture was diluted with ethyl acetate (40 mL), washed with a saturated, aqueous solution of $NaHCO_3$(40 mL), and dried over $Na_2SO_4$. Rotary evaporation followed by purification of the semi-crude material containing both the α and β anomers. The product was isolated as a yellow powder (0.76 g, 86%). This semi-crude product was carried over into the subsequent deprotection reaction.

41
8-Diethylamino-tricyclic-2'-deoxy-β-D-ribonucleoside, 1

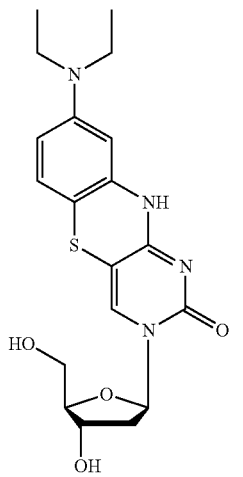

8-Diethylamino-tC 3',5'-di-O-(p-toluoyl)-2'-deoxy-β-D-ribonucleoside 8 (662 mg, 1.03 mmol) was placed in a dry 25 mL round-bottomed flask and suspended in 5 mL of methyl alcohol. To this was added (0.769 mL, 4.13 mmol) of 25% NaOMe in methanol and the reaction was tracked by TLC (10% MeOH in $CH_2C_{12}$) and found to be complete in 18 hrs. The reaction was quenched by the addition of acetic acid (0.236 mL, 4.13 mmol) and the solvent was removed by rotary evaporation. Purification and separation of the α and β anomers was done using flash chromatography and 10% EtOH in $CHCl_3$. The products were isolated as separate anomers in the form of yellow films (168.3 mg total, 39% yield of each of the α and β anomers)$^1$H NMR (400 MHz, MeOD): δ 7.88 (s, 1H), 6.77 (d, J=8.7 Hz, 1H), 6.35 (dd, J=8.5, 2.6 Hz, 1H), 6.32 (d, J=2.5 Hz, 1H), 6.19 (t, J=6.4 Hz, 1H), 4.36 (m, 1H), 3.92 (q, J=3.5 Hz, 1H), 3.82 (dd, J=12.1, 3.1 Hz, 1H), 3.72 (dd, J=12.0, 3.6 Hz, 1H), 3.34 (m, 4H), 2.35 (m, 1H), 2.14 (m, 1H), 1.14 (t, J=6.9 Hz, 6H)$^{13}$C NMR (100 MHz, MeOD): δ 160.6, 156.1, 147.6, 136.7, 134.1, 126.3, 108.3, 100.6, 100.1, 98.7, 87.6, 86.4, 70.3, 61.1, 48.4, 44.0, 11.4. (ESI) cald. for $C_{19}H_{24}N_4O_4S$ [M+H]+ 405.1518, found 405.1623.

42
8-Diethylamino-tC 2'-deoxy-5'-dimethoxytrityl-β-D-ribonucleoside, 9

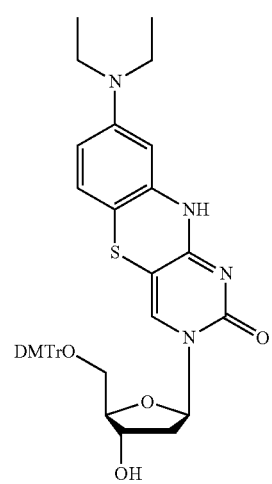

8-Diethylamino-tricyclic-2'-deoxy-β-D-ribonucleoside 1 (129 mg, 3.18 mmol) was placed in a clean dry 25 mL side-armed, round-bottomed flask. To this was added a minimal amount of dry pyridine (about 3 mL) under $N_2$ and dry triethylamine (48.7 µL, 3.50 mmol) was then added, and the reaction mixture stirred for 5 minutes. To this was added dimethoxytritylchloride (118 mg, 3.50 mmol) and the reaction was monitored by TLC (10% MeOH in $CH_2Cl_2$) and found to be complete in 3 hours. The reaction was quenched with MeOH and the solvent was evaporated by rotary evaporation. The crude product was purified by flash chromatography (10% MeOH in $CH_2Cl_2$ with 1% triethylamine). The semi-crude product was obtained and found to contain TEA salts, which were carried directly into the next reaction.

8-Diethylamino-tC 2'-deoxy-5'-dimethoxytrityl-3'-cyanoethyldiisopropyl phosphoramidite-β-D-ribonucleoside, 10

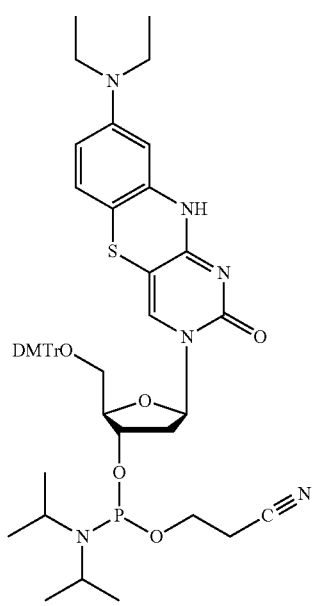

8-Diethylamino-tC 2'-deoxy-5'-dimethoxytrityl-β-D-ribonucleoside 9 (all crude material from the previous step) was placed in a dry 25 mL side-armed, round-bottomed flask under $N_2$. To this was added diisopropylammonium tetrazolide (0.152 mg, 4 eq.) and anhydrous $CH_2Cl_2$ (2 mL). The reaction mixture was stirred for five minutes, and then 2-cyanoethyl-N,N,N',N'-tetraisopropylphosphorodiamidite was added (77.5 μL, 0.244 μmol). The reaction was monitored by TLC (10% MeOH in $CH_2Cl_2$) and found to be complete in 2.5 hours. The solvent was evaporated by rotary evaporation and the crude product was purified by flash chromatography (0 to 100% EtOAc in hexanes with 1% trimethylamine to protect the compound from the acidic nature of the silca). The pure product was isolated as a yellow film (120 mg, 45% over two steps). $^{31}$P NMR (162 MHz, CDCl$_3$): 150.0 149.8: (ESI) cald. for $C_{49}H_{59}N_6O_7PS$ [M+H]+ 907.3904, found 907.3951.

Synthetic Procedures and Data for Fluorescence Turn-on Ribonucleosides

2',3',5'-tri-O-acetyl-8-diethylamino-tC-ribonucleoside. 8-Diethylamino-3H-pyrimido[5,4-b][1,4]benzothiazin-2(10H)-one (15 mg, 0.052 mmol) was dissolved in 1 mL of anhydrous acetonitrile in a dry 25-mL round-bottom flask with magnetic stirring. After adding NO-bis(trimethylsilyl)acetamide (19 μL, 0.078 mmol), the reaction was refluxed at 50° C. for 20 min under $N_2$ and subsequently cooled to room temperature, before adding 1,2,3,5-Tetra-O-acetyl-β-$_D$-ribofuranose (20 mg, 0.062 mmol) and trimethylsilyl trifluoromethanesulfonate (12 μL, 0.068 mmol). The reaction refluxed for 2.5 hours at 50° C. under nitrogen gas. Reaction progress was monitored by TLC with 10% methanol (MeOH) in methylene chloride (DCM). Once the reaction was finished, the flask was cooled to room temperature before transferring to a separation funnel with 8 mL of DCM and 8 mL of 5% NaHCO$_3$ solution. After dispensing the first bottom organic layer, a second 8 mL of DCM was added to extract remaining product from the aqueous phase. The organic phases were combined, dried over anhydrous Na$_2$SO$_4$, and solvent removed by rotary evaporation. The crude mixture was purified by flash chromatography using 5% ethyl acetate in hexanes to yield the product as a yellow film. $^1$H NMR (400 MHz, CD$_3$OD) δ 7.52 (s, 1H), 6.79 (d, J=8.6 Hz, 1H), 6.36 (dd, J=2.7, 8.6 Hz, 1H), 6.34 (d, J=2.5 Hz, 1H), 5.95 (d, J=4.25 Hz, 1H), 5.47 (t, J=4.3, 10.1 Hz, 1H), 5.39 (m, J=5.6, 11.2 Hz, 1H), 4.38 (m, 3H), 3.33 (q, J=7.1 Hz, 4H), 2.18 (s, 3H), 2.12 (s, 3H), 2.11 (s, 3H), 1.14 (t, J=7.1 Hz, 6H).

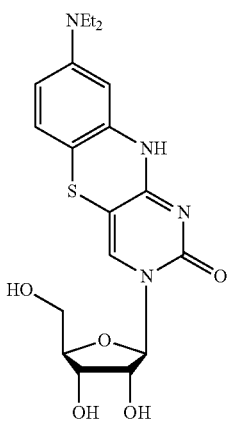

8-diethylamino-tC-ribonucleoside. 2',3',5'-tri-O-acetyl-8-diethylamino-tC-ribonucleoside (12 mg, 0.022 mmol) was dissolved in 1 mL of anhydrous methyl alcohol in a dry 25-mL round-bottom flask with magnetic stirring. After adding 30% NaOMe (15 μL, 0.080 mmol), the reaction was stirred for 1 hour at room temperature and reaction progress monitored by TLC with 10% MeOH in DCM. Once the reaction finished, glacial acetic acid (1.1 μL, 0.02 mmol) was added and the reaction stirred for 5 min prior to solvent removal by rotary evaporation and vacuum oil pump. The crude mixture was suspended in 10% ethanol in chloroform and purified using silica gel chromatography. Fractions containing product were pooled and dried by rotary evaporation and vacuum oil pump to yield the product as a yellow solid. $^1$H NMR (400 MHz, CD$_3$OD) δ 7.96 (s, 1H), 6.75 (d, J=8.7 Hz, 1H), 6.34 (dd, J=8.7 Hz, 1H), 6.32 (d, J=2.6 Hz, 1H), 5.83 (d, J=3.3 Hz, 1H), 4.12 (dd, J=3.3, 6.4 Hz, 2H), 4.00 (dd, J=2.5, 12.3 Hz, 1H), 3.89 (dd, J=2.6, 12.3 Hz, 1H), 3.74 (dd, J=2.8, 6.4 Hz, 1H), 3.45 (q, J=7.0 Hz, 4H), 1.13 (t, J=7.0 Hz, 6H).

Example 2. Oligonucleotide Synthesis and Characterization

Solid phase DNA synthesis to prepare oligonucleotides containing 8-DEA-tC was performed by TriLink BioTechnologies, San Diego, Calif. using standard phosphoramidite conditions and compound 8-DEA-tC amidite 10. The HPLC-purified oligonucleotides were characterized by MALDI-TOF mass spectrometry and found to match the expected molecular weights as shown below. Natural DNA oligonucleotides for the complementary sequences and the AA mismatch and AA complement with the dSpacer abasic site surrogate were obtained from Integrated DNA Technologies, Coralville, Iowa

| Sequence Name | Sequence | Expected Molecular Weight (g/mol) | Mass Spec Analysis (amu) |
|---|---|---|---|
| GA | 5'-CGC-AGX-ATC-G-3' (SEQ ID NO: 10) | 3190.7 | 3190.1 |
| CT | 5'-CGC-ACX-TTC-G-3' (SEQ ID NO: 11) | 3141.8 | 3140.9 |
| GC | 5'-CGC-AGX-CTC-G-3' (SEQ ID NO: 12) | 3166.7 | 3166.5 |
| CA | 5'-CGC-ACX-ATC-G-3' (SEQ ID NO: 13) | 3150.8 | 3150.0 |
| GG | 5'-CGC-AGX-GTC-G-3' (SEQ ID NO: 14) | 3206.7 | 3206.2 |
| CC | 5'-CGC-ACX-CTC-G-3' (SEQ ID NO: 15) | 3126.8 | 3126.0 |
| TA | 5'-CGC-ATX-ATC-G-3' (SEQ ID NO: 16) | 3165.8 | 3165.2 |
| TT | 5'-CGC-ATX-TTC-G-3' (SEQ ID NO: 17) | 3156.8 | 3156.1 |
| AA | 5'-CGC-AAX-ATC-G-3' (SEQ ID NO: 18) | 3174.8 | 3174.2 |

Complementary Sequences

| Sequence Name | Sequence |
|---|---|
| GA complement | 5'-CGA-TGC-TGC-G-3' (SEQ ID NO: 30) |
| CT complement | 5'-CGA-AGG-TGC-G-3' (SEQ ID NO: 31) |
| GC complement | 5'-CGA-GGC-TGC-G-3' (SEQ ID NO: 32) |
| CA complement | 5'-CGA-TGG-TGC-G-3' (SEQ ID NO: 33) |
| GG complement | 5'-CGA-CGC-TGC-G-3' (SEQ ID NO: 34) |
| CC complement | 5'-CGA-GGG-TGC-G-3' (SEQ ID NO: 35) |
| TA complement | 5'-CGA-TGA-TGC-G-3' (SEQ ID NO: 36) |
| TT complement | 5'-CGA-AGA-TGC-G-3' (SEQ ID NO: 37) |
| AA complement | 5'-CGA-TGT-TGC-G-3' (SEQ ID NO: 38) |
| AA mismatch complement | 5'-CGA-TAT-TGC-G-3' (SEQ ID NO: 39) |
| AA abasic site complement | 5'-CGA-T(dSpacer)T-TGC-G-3' (SEQ ID NO: 40) |

Example 3. Computational Details and Molecular Modeling of (8-DEA)tC in a DNA Duplex Calculations were carried out under Gaussian 09 using the B3LYP density functional method and the cc-pVDZ basis set. Geometries were optimized to default convergence criteria, and a natural bond order (NBO) analysis carried out on the molecular orbitals at the optimized geometry. The HOMO and LUMO were rendered using GaussView 5.0.

| tC energy and optimized geometry. Energy = −1444.05026047 hartree | | | |
|---|---|---|---|
| Atomic Number | Coordinates (Angstroms) | | |
| | X | Y | Z |
| 6 | 2.568452 | 0.641700 | −0.490761 |
| 6 | 3.517709 | 0.821847 | 0.696449 |
| 6 | 4.226099 | −0.989618 | −0.721768 |
| 6 | 4.783728 | 0.143063 | 0.166525 |
| 1 | 3.130176 | 0.268019 | 1.565560 |
| 1 | 3.655504 | 1.876678 | 0.964726 |
| 1 | 4.768668 | −0.974689 | −1.682397 |
| 8 | 2.832185 | −0.669164 | −0.966426 |
| 6 | 4.292709 | −2.382293 | −0.110458 |
| 1 | 5.349024 | −2.668315 | 0.016865 |
| 1 | 3.832733 | −3.105585 | −0.811455 |
| 8 | 3.698309 | −2.448115 | 1.177191 |
| 1 | 2.754005 | −2.269075 | 1.056554 |
| 8 | 5.535344 | 0.995233 | −0.695666 |
| 1 | 5.823322 | 1.761315 | −0.177220 |
| 1 | 5.410445 | −0.259188 | 0.981751 |
| 7 | 1.136144 | 0.747608 | −0.171967 |
| 6 | 0.315514 | −0.337786 | −0.135880 |
| 6 | 0.651214 | 2.068162 | 0.091469 |
| 6 | −1.010488 | −0.198472 | 0.165432 |
| 1 | 0.779830 | −1.297617 | −0.354356 |
| 8 | 1.450526 | 2.993807 | 0.092291 |
| 7 | −0.698986 | 2.206846 | 0.304322 |
| 6 | −1.477494 | 1.147084 | 0.340928 |
| 16 | −2.069802 | −1.601326 | 0.470652 |
| 7 | −2.820697 | 1.377408 | 0.533882 |
| 6 | −3.644872 | −0.878070 | 0.027454 |
| 6 | −3.858632 | 0.508688 | 0.159056 |
| 1 | −3.043172 | 2.367765 | 0.581549 |
| 6 | −4.697770 | −1.711682 | −0.362220 |
| 6 | −5.136445 | 1.027545 | −0.095573 |
| 6 | −5.972281 | −1.187777 | −0.594436 |
| 1 | −4.513475 | −2.782262 | −0.473442 |
| 6 | −6.188929 | 0.185266 | −0.457259 |
| 1 | −5.299567 | 2.104721 | −0.004076 |
| 1 | −6.787779 | −1.851991 | −0.885855 |
| 1 | 2.777571 | 1.398616 | −1.264010 |
| 1 | −7.177678 | 0.609765 | −0.641147 |

| 8-DEA-tC energy and optimized geometry. Energy = −1656.64869984 hartree | | | |
|---|---|---|---|
| Atomic Number | Coordinates (Angstroms) | | |
| | X | Y | Z |
| 6 | −4.095977 | 0.766006 | 0.461013 |
| 6 | −5.062165 | 0.931451 | −0.714855 |
| 6 | −5.865898 | −0.708574 | 0.854128 |
| 6 | −6.360619 | 0.390628 | −0.110359 |
| 1 | −4.738644 | 0.291011 | −1.550027 |
| 1 | −5.128197 | 1.971927 | −1.056432 |
| 1 | −6.378955 | −0.575057 | 1.822042 |
| 8 | −4.445879 | −0.481397 | 1.040974 |
| 6 | −6.056924 | −2.135734 | 0.360054 |
| 1 | −7.135369 | −2.346871 | 0.280622 |
| 1 | −5.633556 | −2.834796 | 1.107236 |
| 8 | −5.506978 | −2.350365 | −0.930875 |
| 1 | −4.548379 | −2.238809 | −0.846473 |
| 8 | −7.028761 | 1.360408 | 0.695081 |
| 1 | −7.264069 | 2.106609 | 0.123799 |
| 1 | −7.034392 | −0.025393 | −0.879934 |
| 7 | −2.670123 | 0.736044 | 0.102282 |
| 6 | −1.931189 | −0.407931 | 0.142151 |
| 6 | −2.098340 | 1.988750 | −0.284485 |
| 6 | −0.608393 | −0.395749 | −0.201212 |
| 1 | −2.457140 | −1.308123 | 0.454141 |
| 8 | −2.828158 | 2.969702 | −0.343270 |
| 7 | −0.750042 | 2.007162 | −0.543050 |
| 6 | −0.050613 | 0.892166 | −0.506175 |
| 16 | 0.339190 | −1.890873 | −0.419445 |
| 7 | 1.297743 | 1.007196 | −0.753928 |
| 6 | 1.968675 | −1.241436 | −0.063470 |
| 6 | 2.283832 | 0.101795 | −0.323053 |
| 1 | 1.584905 | 1.971826 | −0.892203 |
| 6 | 2.990561 | −2.087469 | 0.374295 |
| 6 | 3.593944 | 0.566269 | −0.149781 |
| 6 | 4.297706 | −1.636762 | 0.532887 |
| 1 | 2.760322 | −3.133956 | 0.586144 |
| 6 | 4.637331 | −0.282732 | 0.286559 |
| 1 | 3.782407 | 1.615367 | −0.370958 |
| 1 | 5.047839 | −2.349562 | 0.868056 |
| 7 | 5.931206 | 0.201007 | 0.500190 |
| 6 | 7.051870 | −0.740688 | 0.481710 |
| 6 | 6.203796 | 1.604033 | 0.175226 |
| 1 | 7.913824 | −0.248849 | 0.950615 |
| 1 | 6.815430 | −1.586676 | 1.143137 |
| 6 | 7.438334 | −1.250053 | −0.912364 |
| 1 | 6.136118 | 1.786045 | −0.918795 |
| 1 | 5.405944 | 2.206508 | 0.636606 |

8-DEA-tC energy and optimized geometry.
Energy = −1656.64869984 hartree

| Atomic Number | Coordinates (Angstroms) | | |
|---|---|---|---|
| | X | Y | Z |
| 6 | 7.536988 | 2.139974 | 0.693392 |
| 1 | 6.598169 | −1.774367 | −1.394118 |
| 1 | 7.741869 | −0.420517 | −1.572205 |
| 1 | 8.285541 | −1.952633 | −0.844155 |
| 1 | 7.648285 | 1.964242 | 1.775396 |
| 1 | 8.407237 | 1.706280 | 0.177858 |
| 1 | 7.568725 | 3.227613 | 0.523661 |
| 1 | −4.225743 | 1.591865 | 1.179395 |

Example 4. UV/Vis and Fluorescence Spectra and Quantum Yield Determinations

All photophysical experiments were measured in a quartz sub-micro cuvette (10 mm path length) purchased from Starnacell Inc. Solutions were prepared in 1×PBS buffer at pH 7.4. Steady state emission scans were recorded using a PTI QuantaMaster QM-400 and absorbances were measured on a Shimadzu UV-1700 Pharmaspec spectrometer. Quantum yield measurements were performed the comparative method of Williams et. al. and measured in duplicate, at minimum.[7] Quinine sulfate in 0.1M $H_2SO_4$ was used as a reference standard for all photophysical measurements. Measurements by using a commercial sample of pyrrolo-dC to obtain a fluorescence quantum yield of 0.046, matching the value of 0.05 as reported by the Tor group were validated.[8] All measurements were taken with an absorbance range of 0.01-0.1. Subsequent dilutions were performed stepwise in order to obtain a minimum of five absorbance and emission spectra for quantum yield determinations. Representative data from these quantum yield measurements is plotted below. Quantum yield determinations were obtained using the following equation:

$$\phi_X = \phi_{Std}\left(\frac{Slope_X}{Slope_{Std}}\right)\left(\frac{\eta_X^2}{\eta_{Std}^2}\right)$$

The determination of quantum yields for single-stranded oligonucleotides containing 8-DEA tC were calculated using the integrated emission intensity measurements of the single strand prior to the addition of the complementary strand, with the following equation. This method was validated by comparison with and confirmed with a SS quantum yield experiment.

$$SS\phi = DS\phi \times \frac{SS\ EMInitial}{DS\ EMInitial} \times \frac{DS\ ABS}{SS\ ABS} \times \frac{DS\ Total\ Vol}{SS\ Total\ Vol}$$

Samples of double-stranded oligonucleotides were prepared using a known concentration of single-stranded oligonucleotide and adding a total of 2.4 equivalents of complementary strand at room temperature. A single-strand absorbance and emission were taken prior to the addition of the first 1.2 equivalents of complementary strand for purposes of single-strand calculation and verification of hybridization. An additional 1.2 equivalent is added after the first double-strand to ensure that complete hybridization was achieved. Thermal annealing procedures had no effect on the measurements as expected, given that these sequences were chosen to have no competing, stable secondary structures.

Normalized absorption and emission plots of single-stranded oligonucleotides and double-stranded oligonucleotides in 1×PBS buffer at pH 7.4 were determined accordingly.

Example 5. Viscosity Sensitivity Measurements

The responsiveness of (8-DEA)tC, tC, and 9-(2,2-dicyanovinyl)julolidine (DCVJ) to viscosity changes using binary methanol-glycerol mixtures was determined.

Molecular rotors are known to have fluorescent properties that are dependent on the medium viscosity, the fluorescence spectra of parent tC and (8-DEA)tC were examined in methanol-glycerol mixtures ranging from 0 to 100% methanol in glycerol at 25° C. These spectra were compared to a known molecular rotor DCVJ with well characterized properties.

Viscosity [cp] was calculated using equation:

$$\log \eta_{mix} = x_1 \log \eta_1 + x_2 \log \eta_2$$

| | |
|---|---|
| η: Solvent viscosity | $x_n$: Volume fractions of each solvent. |

The preparation of ten separate samples of the same concentrations with varying binary viscosity mixtures of MeOH:Glycerol were prepared. Special care had to be taken in the preparation of the mixtures that contained 50% Glycerol and above. Due to its very viscous nature heat was applied (~45° C.) for about 1 hr to aid in the thorough mixing of the solution being studied.

The solvent mixtures span a viscosity range from 0.538 cP to 1317 cP.

A calibration plot of fluorescence intensity (I) versus viscosity (η) were constructed using the Foster-Hoffman equation $\Phi_F = z\eta^\alpha$, relating the fluorescence quantum yield ($\Phi_F$) as a function of viscosity (η) and fluorophore and solvent-specific constants (z, α).

The Simplified Relationship:

$$\text{Log}(I) = C + x \log(\eta)$$

| | |
|---|---|
| I: fluorescence emission intensity | η: solvent viscosity |
| X: dye-dependent constant | C: temperature-dependent constant. |

Derived from the Foster-Hoffman relation, a clear correlation between fluorescence intensity and viscosity of the solvent mixture was established. The viscosity of the sample seemed to have a minimal impact on the compounds absorbance spectra with greater implications in the fluorescence spectra.

Viscosity of binary methanol-glycerol mixtures.

| Volume Ratio Methanol:Glycerol | Viscosity [cp] |
|---|---|
| 1:0 | 0.583 |
| 0.9:0.1 | 1.84 |
| 0.8:0.2 | 5.14 |
| 0.7:0.3 | 13.03 |
| 0.6:0.4 | 30.27 |
| 0.5:0.5 | 65.27 |
| 0.4:0.6 | 131.85 |

-continued

| Volume Ratio Methanol:Glycerol | Viscosity [cp] |
|---|---|
| 0.3:0.7 | 251.50 |
| 0.2:0.8 | 456.01 |
| 0.1:0.9 | 790.60 |
| 0:1 | 1317.00 |

Example 6. Stern-Volmer Analysis

In order to assess the magnitude that chloride, present in our buffers, would quench the fluorescent cytidine analogues, a Stern-Volmer analysis was performed spanning from 0 mM NaCl to 180 mM NaCl to mimic the environment of the 1XPBS buffer used in the fluorescence measurements of the oligomers.

A solution fluorophore was prepared and a known volumes of a 0.5 M NaCl solution were titrated in and the resulting fluorescence change was measured. The dilution factor was taken into account when calculating integrated fluorescence intensity.

Example 7. Circular Dichroism and Melting Temperature Measurements

UV CD spectra of oligonucleotide duplexes at a concentration of 5 µM in phosphate buffered saline (10 mM sodium phosphate, pH 7.4, 27 mM potassium chloride, 137 mM sodium chloride) were collected at 25° C. in a 1 cm path length cell on an Aviv model 420 spectrophotometer equipped with a Peltier temperature controller. Background-subtracted spectra were smoothed and normalized to concentration using A260 nm as calculated from detector voltage using the following equation and converted to standard units.

$$Abs = \log\left(\frac{Voltage_{sample}}{Voltage_{solvent}}\right) * 7.4$$

Figure 8:
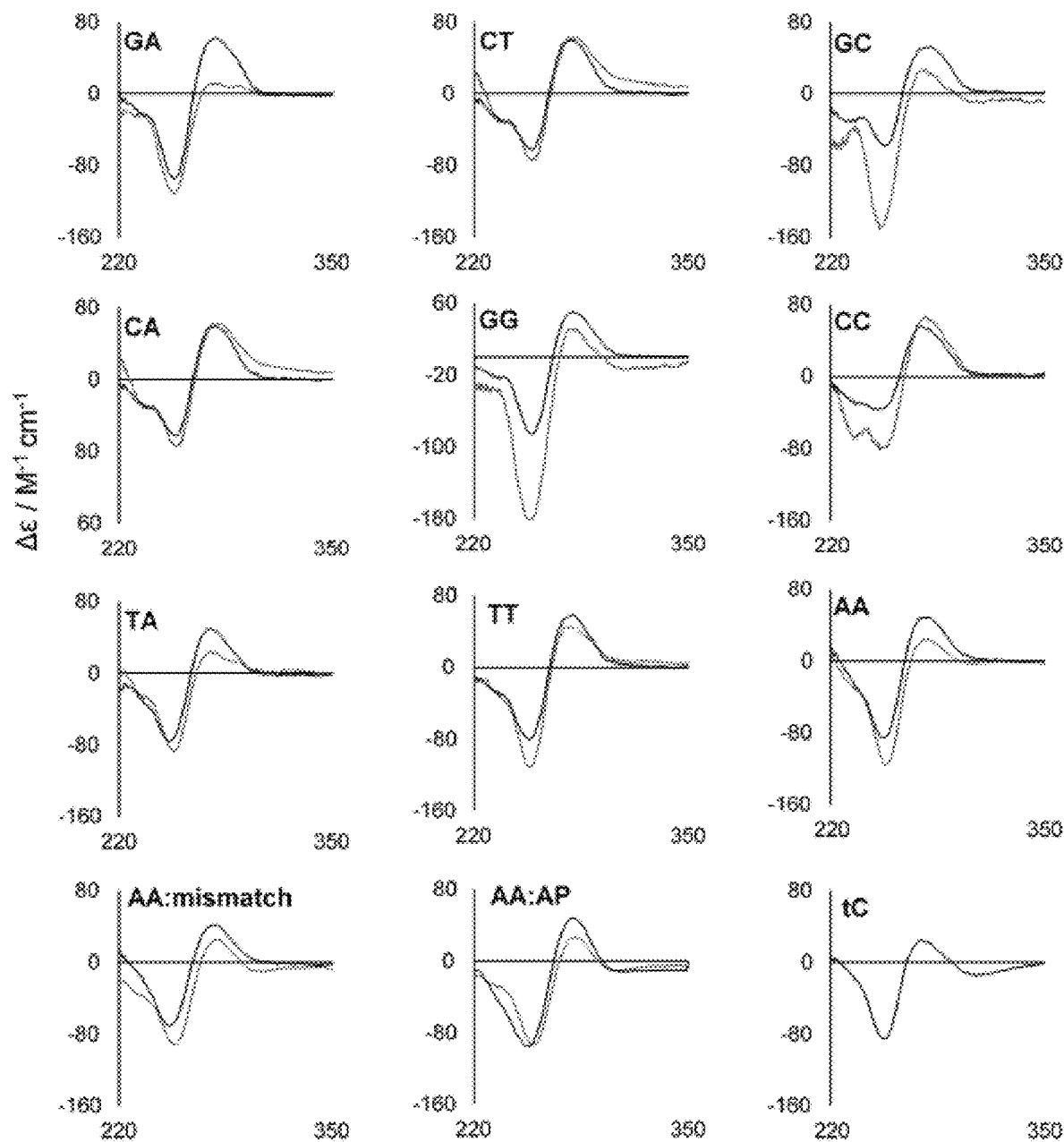
FIG. 8. CD Spectra of duplex oligonucleotides at 5 µM in 1xPBS from 350 to 220 nm. Oligonucleotide duplexes incorporating 8-DEA-tC (red) or cytosine (black) and neighboring 5' and 3' bases as named in the main text. The bottom right panel is of the duplex containing tC and neighboring bases AA.
Figure 9:
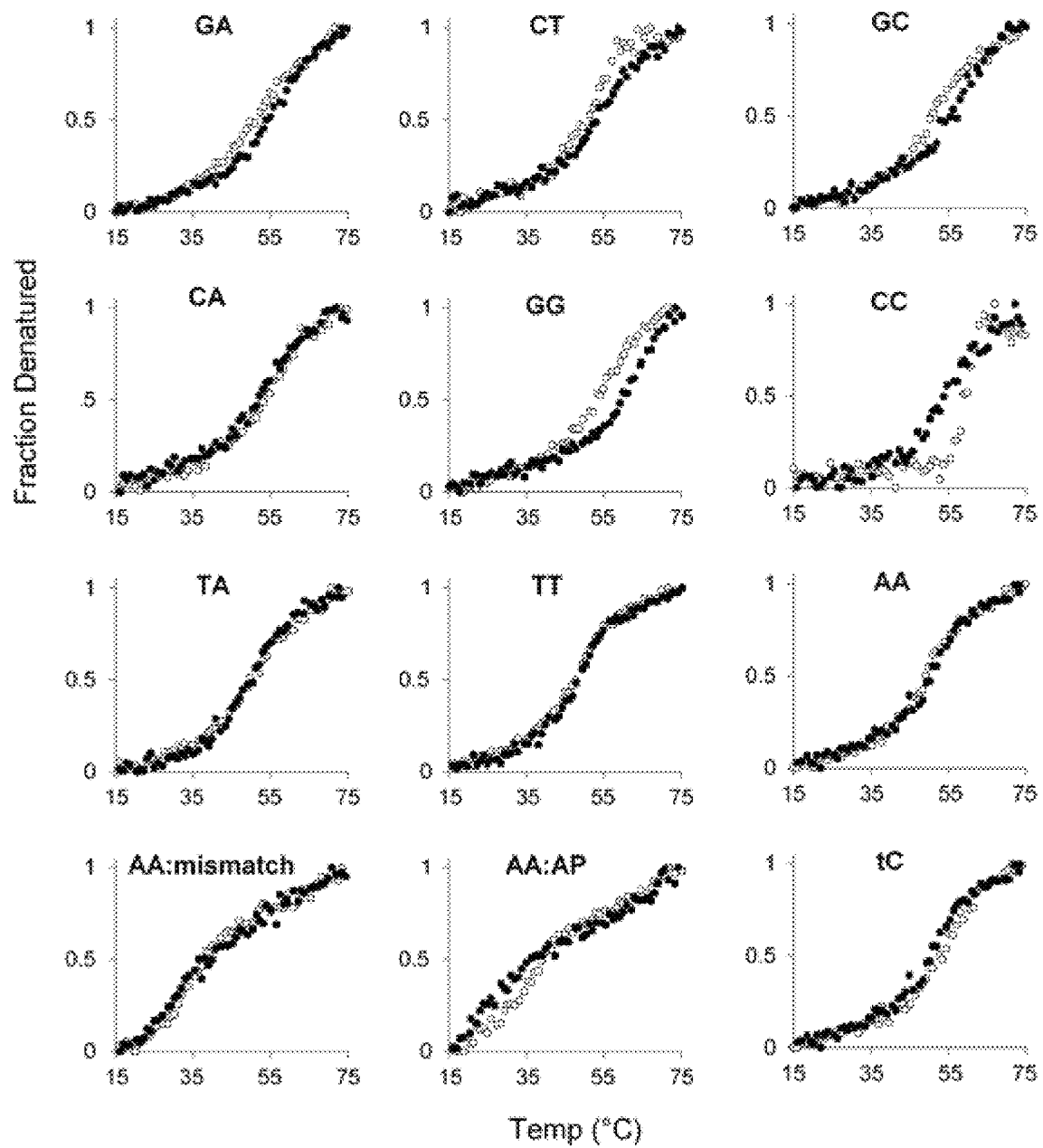
FIG. 9. CD melting curves at 255 nm for 8-DEA-tC oligonucleotides (open circles) and native DNA duplexes (closed circles). tC is plotted next to native AA.
Figure 10A:
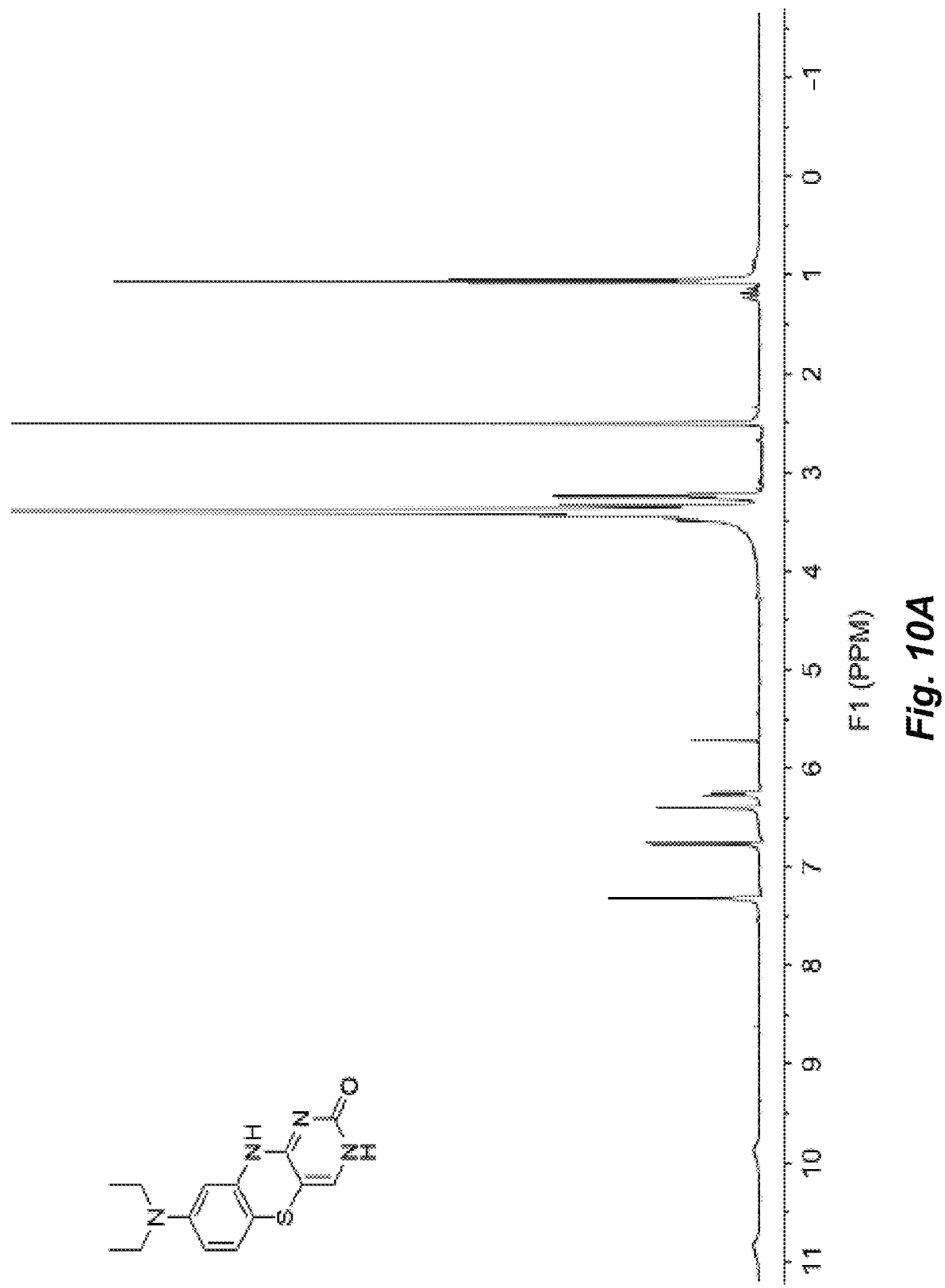
FIG. 10A-10D. NMR Spectra of selected compounds.
Figure 10B:
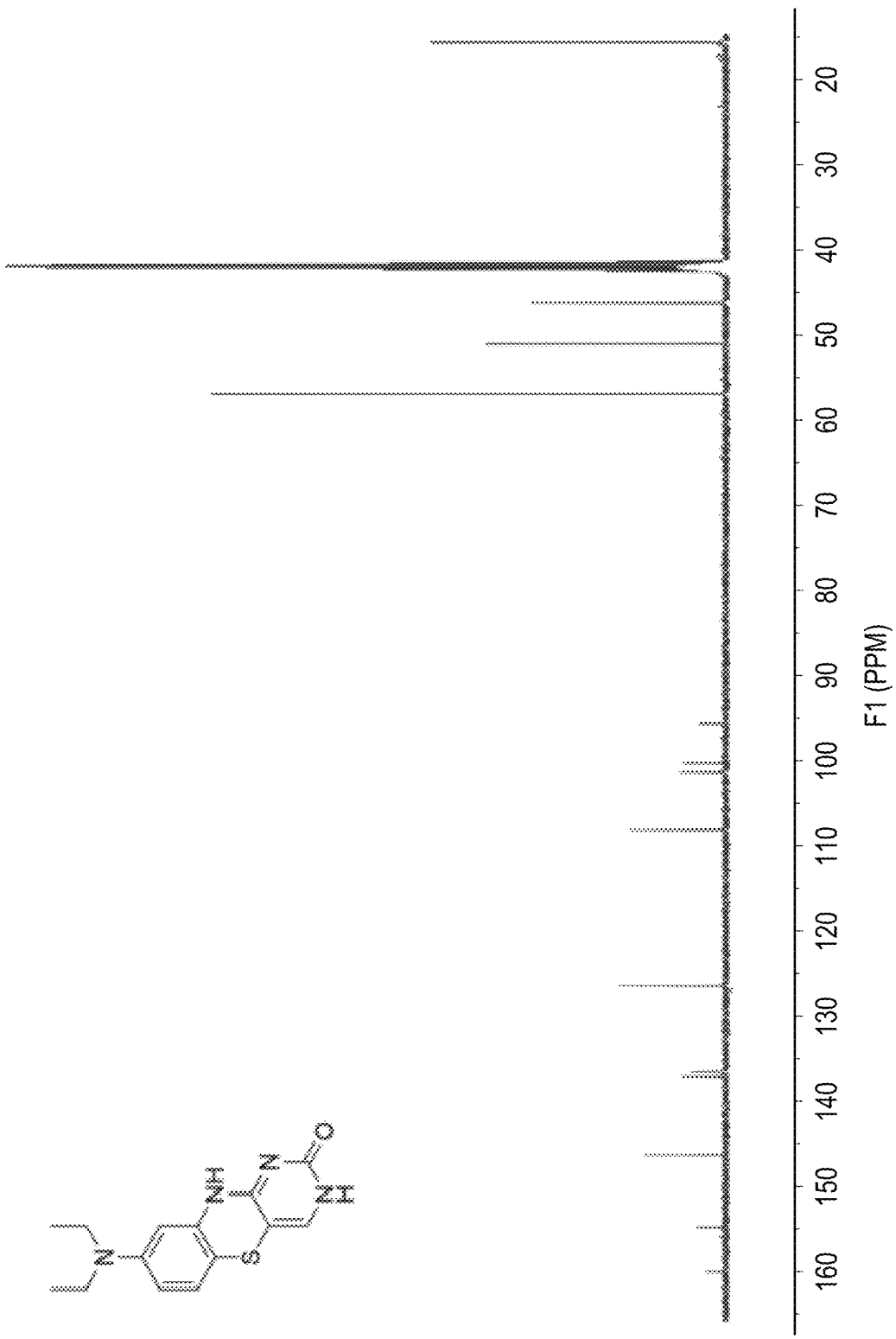
Figure 10C:
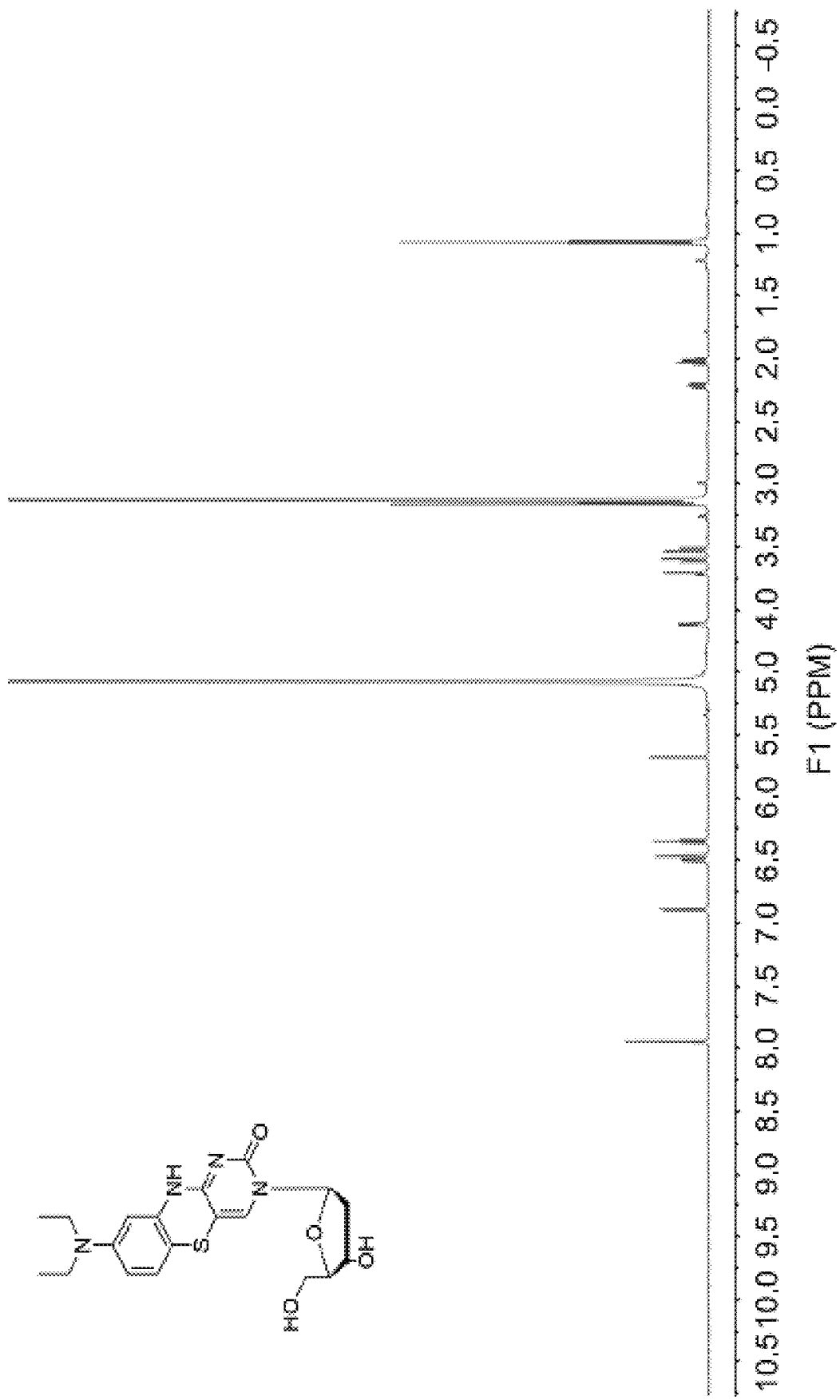
Figure 10D:
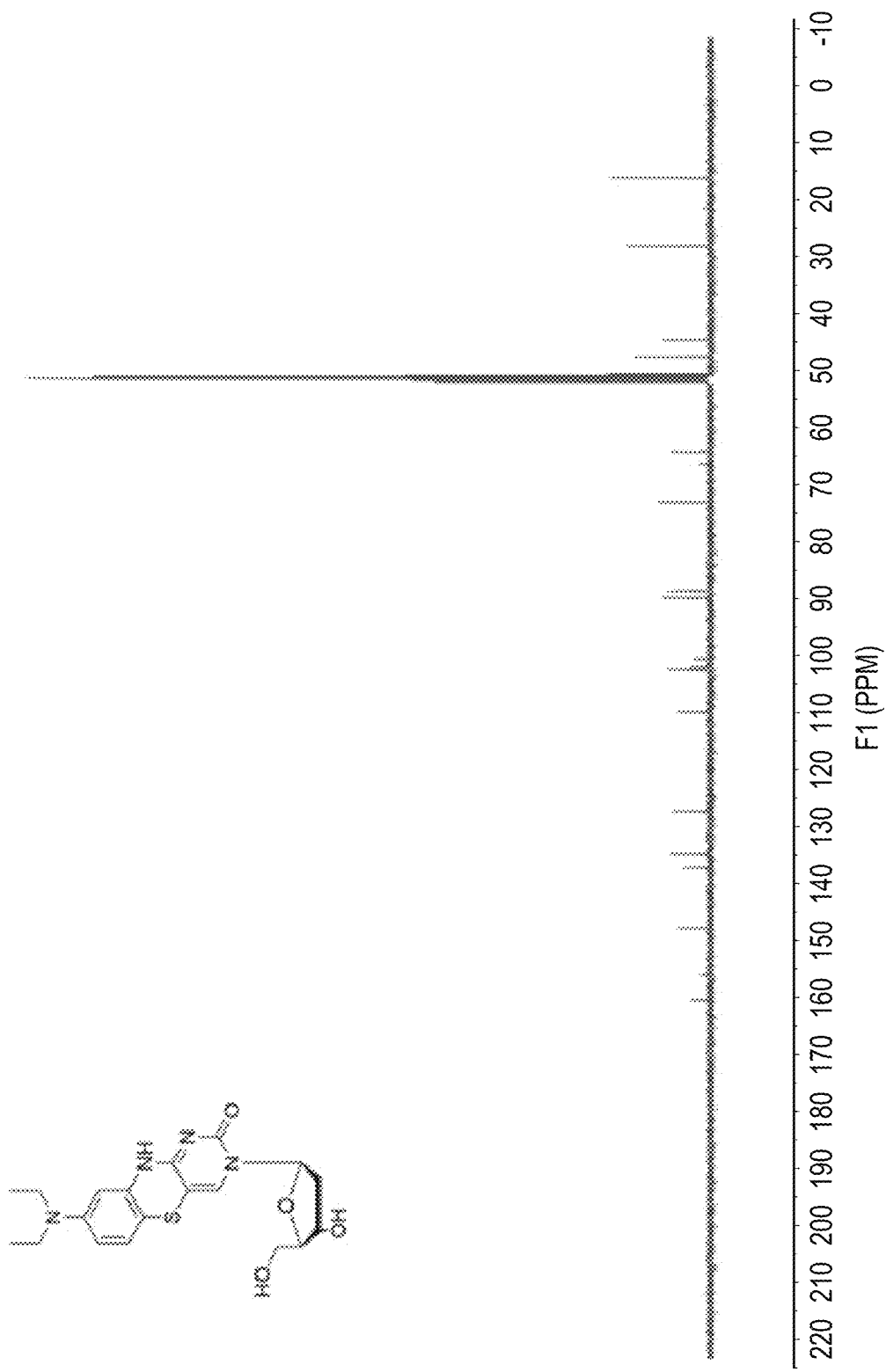

Elipticity at 255 nm was monitored from 15° C. to 75° C. at 1° C. increments. The TM of each duplex was calculated by fitting the raw data to a two-state model in Igor Pro. Melting curves are reported as fraction unfolded.

$$\alpha_U = \frac{\theta_i - \theta_F}{\theta_U - \theta_F}$$

Where θ is ellipticity in mdeg and subscripts U and F indicate signals of strand-separated and duplex DNA, respectively. FIG. 8 shows CD spectra of duplex oligonucleotides at 5 µM in 1×PBS from 350 to 220 nm. Oligonucleotide duplexes incorporating 8-DEA-tC (red) or cytosine (black) and neighboring 5' and 3' bases as named in the main text. The bottom right panel is of the duplex containing tC and neighboring bases AA. FIG. 9 shows CD melting curves at 255 nm for 8-DEA-tC oligonucleotides (open circles) and native DNA duplexes (closed circles). tC is plotted next to native AA.

Example 8. Signal Amplification Using Magnetic Beads for Sample Enrichment

A signal amplification approach described herein involves a simple protocol beginning with lower-fidelity sample enrichment followed by high-fidelity sample analysis using the 8-DEA-tC oligonucleotide probes. An example procedure for DNA (or RNA) enrichment is shown in FIG. 13. The enrichment reagent can be, for example, a DNA oligonucleotide complementary to the target sequence and functionalized with biotin at the 3'-terminus (the choice of terminus is arbitrary for this purpose). This enrichment reagent can be combined with a sample and annealed to the target DNA or RNA. After annealing, the enrichment reagent-target complex can be captured on streptavidin-coated magnetic beads using standard buffer conditions for biotin-streptavidin binding. These beads are widely available commercially, e.g. Dynabeads from ThermoFisher Scientific. After incubation in microfuge tubes, the tubes can be transferred to a magnetic rack causing the beads to migrate and adhere to the magnet-facing side of the tube, leaving the crude sample residue to be discarded. As in conventional purification procedures, the cluster of beads can be washed with buffer. Rinsing the bead particles with a minimal volume of elution buffer at elevated temperature can liberate the target sequences from the sequestered enrichment reagent strands, which will be retained by their very strong binding to streptavidin. The highly enriched target samples can then be cooled and the 8-DEA-tC hybridization probes can be introduced to recognize the target with high affinity and specificity. From this point, the target can be quantified against the calibration curves to provide highly sensitive detection.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

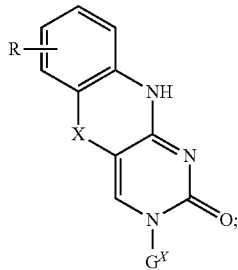

(I)

wherein

R is $OR^1$, or $NR^2R^3$, wherein R is at the ortho, meta, meta', or para position relative to the NH substituent of Formula I;

X is O, C=O, $NR^4$, S, S=O, or $S(=O)_2$;

$G^x$ is a moiety of Formula X1 or X2;

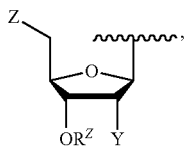

(X1)

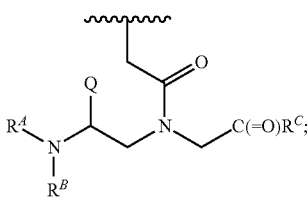

(X2)

Y is H, OH, halo, or Me;

Z is OH, O(dimethoxytrityl), guanidinium, phosphate, diphosphate, triphosphate, phosphoramidite, phosphorothioate, or —$O_2$P(=O)(3'-X1A) wherein Formula X1A is,

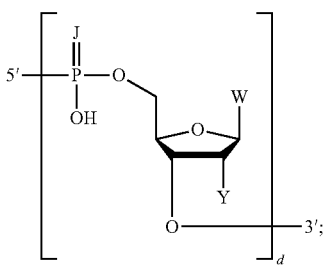

(X1A)

$R^z$ is H, —P(N($R^4$)$_2$)(OCH$_2$CH$_2$CN), or —$O_2$P(=O)(5'-X1A);

$R^1$ is CH$_2$CH$_3$ or (C$_3$-C$_{12}$)alkyl wherein alkyl is optionally branched;

$R^2$ and $R^3$ are each independently $CH_3$, $CH_2CH_3$, or $(C_3-C_{12})$alkyl wherein alkyl is optionally branched;

$R^4$ is H, $CH_3$, or $CH_2CH_3$, $CH(CH_3)_2$;

each Q is independently H, $CH_3$, $CH_2CH_3$, $(C_3-C_{12})$alkyl wherein alkyl is optionally branched, or $-(CH_2CH_2O)n(C_1-C_4)$alkyl where n is 1-20, and when Q is not H the carbon of the CH—Q bond is a stereocenter having an (R)-configuration, or an (S)-configuration;

$R^A$ is H, $CH_3$, $CH_2CH_3$, $(C_3-C_{12})$alkyl wherein alkyl is optionally branched, or an amide bond to X2A wherein Formula X2A is:

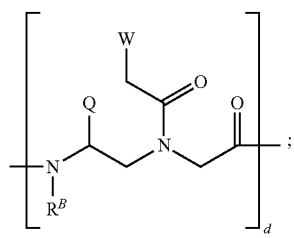

(X2A)

$R^B$ is H, $CH_3$, $CH_2CH_3$, $(C_3-C_{12})$alkyl wherein alkyl is optionally branched, or a protecting group;

$R^C$ is OH, $OCH_3$, $OCH_2CH_3$, $O(C_3-C_{12})$alkyl wherein alkyl is optionally branched, or an amide bond to X2A;

each J is independently O or S, and when J is S the phosphorous stereocenter has an (R)-configuration, or an (S)-configuration;

each W is independently adenine (A), thymine (T), cytosine (C), guanine (G), or Formula IA, wherein Formula IA is,

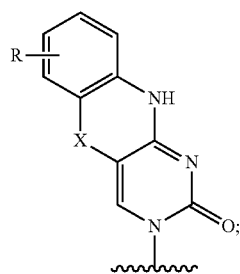

(IA)

and d is 1 to about 50.

2. The compound of claim 1 wherein R is $NR^2R^3$.

3. The compound of claim 2 wherein $R^2$ and $R^3$ are each independently methyl, ethyl, propyl, isopropyl, cyclopropyl.

4. The compound of claim 2 where the substituent R is meta, meta', or para to the NH substituent of Formula I.

5. The compound of claim 1 wherein R is $NR^2R^3$; and X is O, or S.

6. The compound of claim 5 wherein X is S.

7. The compound of claim 5 wherein R is meta-N$(CH_2CH_3)_2$, X is S, and Formula IA is moiety IB, wherein moiety IB is,

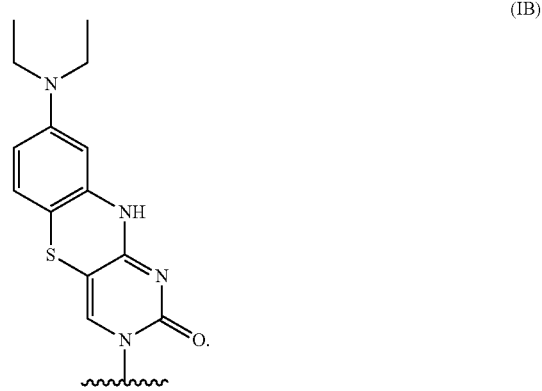 [SMILES: *n1cc2c(nc1=O)Nc1cc(N(CC)CC)ccc1S2]

(IB)

8. The compound of claim 1 wherein $G^X$ is X2 or X2A, and Q is H, $CH_3$, $CH_2CH_3$, $CH_2CH_2CH_3$, $CH(CH_3)_2$, or $-(CH_2CH_2O)n(C_1-C_4)$alkyl, where n is 1-20.

9. The compound of claim 1 wherein $G^X$ is X2, $R^B$ is H, and $R^A$ is H, $CH_3$, $CH_2CH_3$, $CH_2CH_2CH_3$, $CH(CH_3)_2$, carboxybenzyl (Cbz), or tert-butyloxycarbonyl (Boc); or $G^X$ is X2A and $R^B$ is H.

10. The compound of claim 1 wherein the compound is a compound of Formula II:

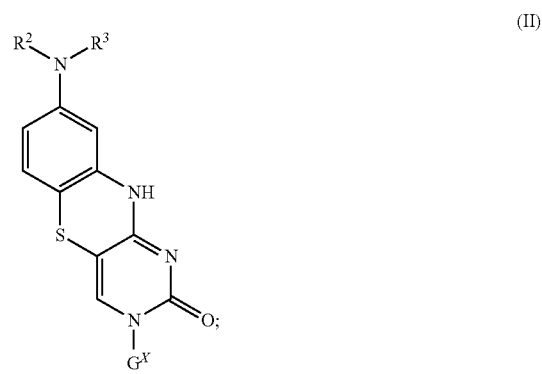

(II)

wherein

Y is H, OH, F, Cl, or Me;

Z is OH, O(dimethoxytrityl), phosphate, triphosphate, or $-O_2P(=O)(3'-X1A)$;

$R^Z$ is H, $-P(N(CH(CH_3)_2)_2)(OCH_2CH_2CN)$, or $-O_2P(=O)(5'-X1A)$;

$R^2$, and $R^3$ are each independently $CH_3$, $CH_2CH_3$, propyl, isopropyl, or cyclopropyl;

Q is H, $CH_3$, $CH_2CH_3$, $CH_2CH_2CH_3$, or $CH(CH_3)_2$;

$R^A$ is H, $CH_3$, $CH_2CH_3$, $CH_2CH_2CH_3$, $CH(CH_3)_2$, or an amide bond to X2A;

$R^C$ is OH, $OCH_3$, $OCH_2CH_3$, or an amide bond to X2A; and d is 1-20.

11. The compound of claim 10 wherein the compound is 8-DEA-tC, compound 2, a compound of Formula X3, or a compound of Formula X4:
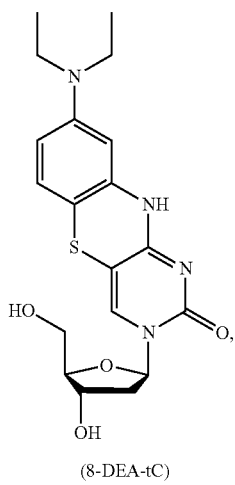
(8-DEA-tC)
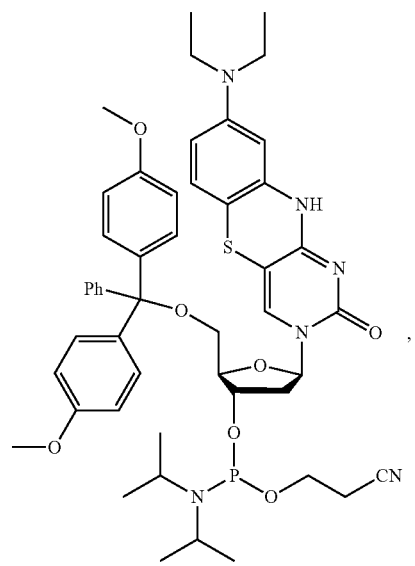
(2)
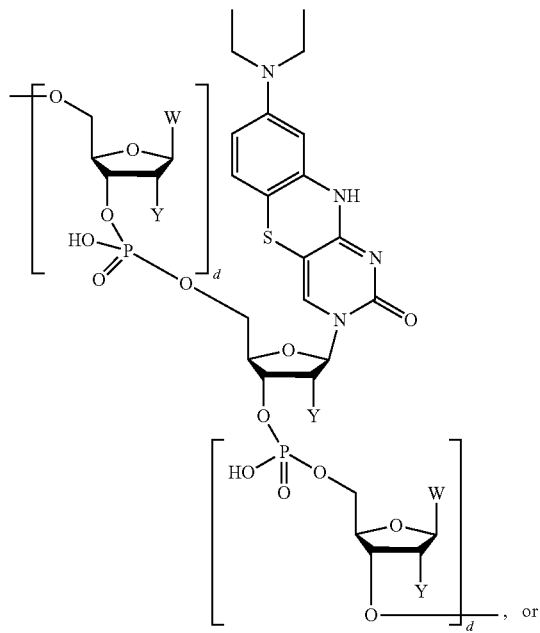
(X3)
, or -continued (X4)

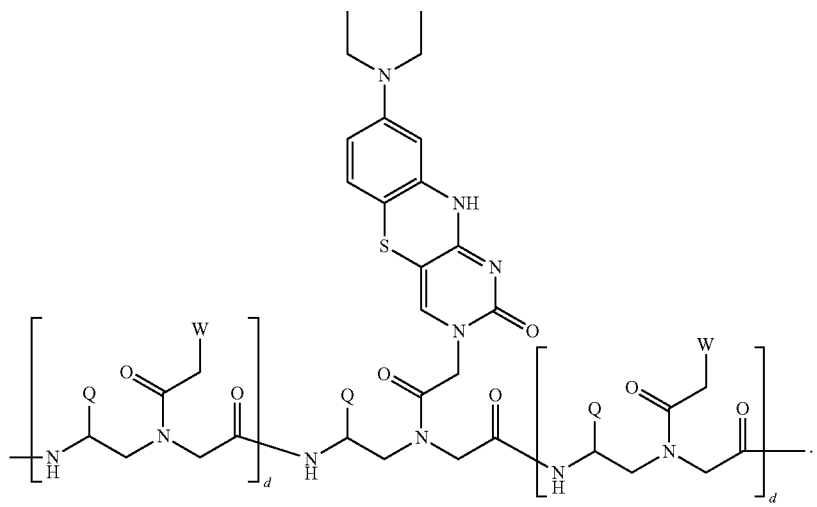

12. The compound of claim 10 wherein the compound is a compound of Formula III:

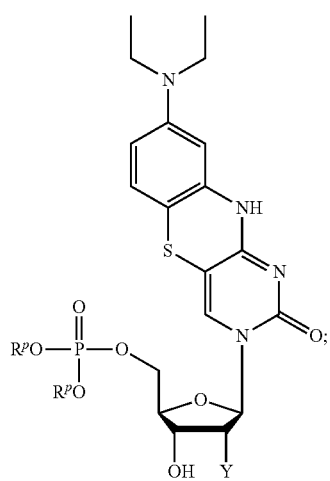

(III)

wherein

Y is H or OH; and each $R^P$ is independently H, phosphate, diphosphate, alkyl, aryl, or a masking group, wherein the masking group is hydrolysable by cytoplasmic esterases inside a cell; and optionally each $OR^P$ is independently an amino moiety.

13. The compound of claim 12 wherein the compound is a compound of Formula X5, a compound of Formula X6, or a compound of Formula X7:

(X5)

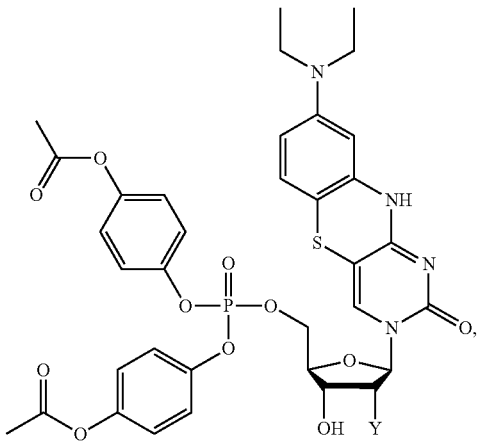

(X6)

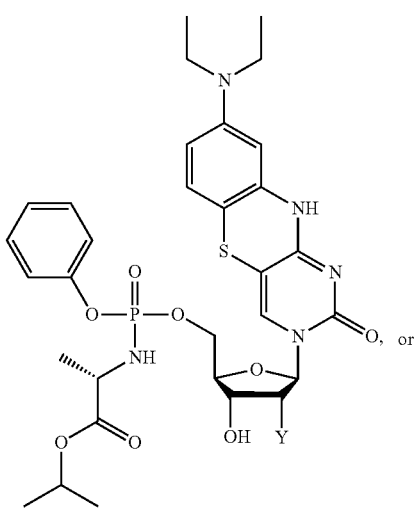

, or

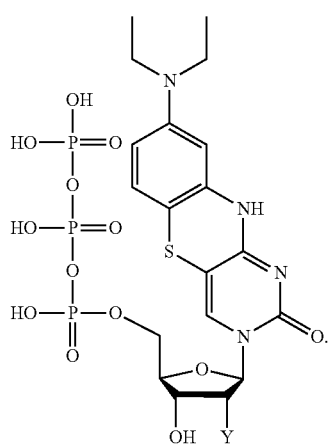
(X7)

14. A method of quantifying nucleic acid synthesis in a cell, the method comprising:
   a) incorporating a compound of claim 1 into the DNA or RNA of a cell, wherein the compound is optionally introduced into a cell by transfecting the cell with a plasmid encoding a nucleotide transporter protein, wherein the compound of claim 1 is a compound that comprises a nucleoside triphosphate;
   b) optionally exposing the cell to a chemical transfection agent, or applying electroporation, wherein the compound of claim 1 is a compound that comprises a nucleoside triphosphate;
   c) detecting a fluorescent signal during nascent DNA or RNA synthesis, wherein the signal is optionally detected by fluorescence microscopy;
   d) quantifying the signal, wherein duplex formation of the compound with the DNA or RNA of the cell provides an increase in fluorescence when the tricyclic cytosine moiety of the compound is based-paired with moiety G in the nucleic acids of the cell; and
   e) assessing cell parameters, wherein the cell parameters comprise cytotoxicity, cell permeability, viral replication, metabolic activity, DNA synthesis, transcription rates, kinetics, rate constants, half-life, or a combination thereof;
   wherein said cell parameters are assessed by quantifying the nucleic acid synthesis in a cell.

15. A method of differentiating nucleic acid sequences, the method comprising:
   a) incorporating a compound of claim 1 into a sample comprising DNA or RNA wherein the compound is a DNA probe or RNA probe of Formula I wherein Z is —O$_2$P(=O)(3' -X1A) and R$^Z$ is —O$_2$P(=O)(5'—X1A), or wherein the compound is peptide nucleic acid (PNA) probe of Formula I wherein R$^A$ is X2A and R$^C$ is X2A, and the DNA, RNA or PNA probe has a specific sequence that is complementary to the sample DNA or RNA;
   b) detecting a fluorescent signal, wherein the signal is optionally detected by fluorescence microscopy;
   c) quantifying the signal, wherein duplex formation of the DNA, RNA, or PNA probe with the sample DNA or RNA provides an increase in fluorescence when the tricyclic cytosine moiety of the DNA, RNA, or PNA probe is based-paired with moiety G of the sample DNA or RNA; and
   d) identifying differentiated DNA or RNA sequences in the sample;
   wherein duplex formation of the DNA, RNA, or PNA probe with a complementary sequence of sample DNA or RNA differentiates the complementary nucleic acid sequence of sample DNA or RNA from a non-complementary sequence of sample DNA or RNA.

16. A method of quantifying the progression of a polymerase chain reaction (PCR), the method comprising:
   a) incorporating a compound of claim 1 into a DNA or RNA primer for a PCR reaction, replacing natural (d)CTP with a compound of claim 1 in the PCR reaction, or a combination thereof, wherein DNA or RNA is amplified;
   b) detecting a fluorescent signal;
   c) quantifying the signal, wherein duplex formation of the compound with the DNA or RNA provides an increase in fluorescence when the tricyclic cytosine moiety of the compound is based-paired with moiety G of the DNA or RNA; and
   d) tracking the amplified RNA or DNA;
   wherein the progression of the PCR is quantified.

17. A method of detecting nucleic acids, the method comprising:
   a) combining a compound of claim 1 that has been incorporated into an oligonucleotide, and a sample comprising DNA or RNA in a solvent to form a mixture;
   b) detecting a fluorescent signal from the mixture, wherein the signal is optionally detected by fluorescence microscopy;
   c) quantifying the signal, wherein duplex formation of the compound with the DNA or RNA provides an increase in fluorescence when the tricyclic cytosine moiety of the compound is based-paired with moiety G of the DNA or RNA; and
   d) comparing the quantum yield to a control sample wherein the control sample comprises the compound of claim 1;
   wherein the presence or absence of double-stranded DNA or RNA is determined.

18. The method of claim 17 wherein quantifying the signal comprises measuring a quantum yield, or visualizing an increase in the brightness of fluorescence.

19. The method of claim 17 wherein the solvent comprises an aqueous buffer for DNA or RNA duplex formation.

20. The method of claim 17 wherein the solvent comprises aqueous phosphate buffered saline (PBS), or 1,4-dioxane.

* * * * *

UNITED STATES PATENT AND TRADEMARK OFFICE
CERTIFICATE OF CORRECTION

| | |
|---|---|
| PATENT NO. | : 11,981,702 B2 |
| APPLICATION NO. | : 17/943682 |
| DATED | : May 14, 2024 |
| INVENTOR(S) | : Byron W. Purse et al. |

It is certified that error appears in the above-identified patent and that said Letters Patent is hereby corrected as shown below:

In the Claims

In Claim 1, at Column 63, Line 9, delete "(5)-configuration" and replace with -- (S)-configuration -- therefor.

Signed and Sealed this
Ninth Day of July, 2024

Katherine Kelly Vidal
*Director of the United States Patent and Trademark Office*